United States Patent
Taylor et al.

(10) Patent No.: US 11,351,392 B2
(45) Date of Patent: Jun. 7, 2022

(54) METHODS, SYSTEMS, AND DEVICES FOR POST-BIRTH RECOVERY

(71) Applicant: My Mommy Magic, LLC, Peoria, AZ (US)

(72) Inventors: Heather Taylor, Peoria, AZ (US); David G. Brinkerhoff, Peoria, AZ (US)

(73) Assignee: MY MOMMY MAGIC, LLC, Peoria, AZ (US)

( * ) Notice: Subject to any disclaimer, the term of this patent is extended or adjusted under 35 U.S.C. 154(b) by 0 days.

(21) Appl. No.: 17/067,089

(22) Filed: Oct. 9, 2020

(65) Prior Publication Data
US 2022/0111223 A1    Apr. 14, 2022

(51) Int. Cl.
*A61N 2/06* (2006.01)
*A61N 2/00* (2006.01)

(52) U.S. Cl.
CPC ............. *A61N 2/008* (2013.01); *A61N 2/002* (2013.01)

(58) Field of Classification Search
CPC . A61N 2/00; A61N 2/02; A61N 2/002; A61N 2/004; A61N 2/006; A61N 2/008
USPC ....................................................... 600/9–15
See application file for complete search history.

(56) References Cited

U.S. PATENT DOCUMENTS

| | | | |
|---|---|---|---|
| 2004/0210254 A1* | 10/2004 | Burnett | A61N 1/40 607/2 |
| 2010/0210894 A1* | 8/2010 | Pascual-Leone | A61N 2/02 600/14 |
| 2014/0330067 A1* | 11/2014 | Jordan | A61N 2/02 600/13 |
| 2018/0125416 A1* | 5/2018 | Schwarz | A61B 5/1128 |
| 2020/0289837 A1* | 9/2020 | Lowin | A61B 5/6803 |

OTHER PUBLICATIONS

Khooshideh, M., et al., Pulsed Electromagnetic Fields for Postsurgical Pain Management in Women Undergoing Cesarean Section, A Randomized, Double-Blind, Placebo-controlled Trial; *Clinical Journal of Pain*, vol. 33, No. 2, Feb. 2017, pp. 142-147.

* cited by examiner

*Primary Examiner* — Samuel G Gilbert
(74) *Attorney, Agent, or Firm* — Ray Quinney & Nebeker; Paul N. Taylor

(57) ABSTRACT

A pulsed electromagnetic field (PEMF) device includes at least one electromagnetic (EM) field emitter. During post-birth recovery, a patient applies the EM field emitter to herself. The PEMF device performs a recovery cycle. In the recovery cycle, the EM field emitter emits EM fields having frequency combinations with a response frequency and a target frequency for a frequency combination period.

19 Claims, 5 Drawing Sheets

METHODS, SYSTEMS, AND DEVICES FOR POST-BIRTH RECOVERY

CROSS-REFERENCE TO RELATED APPLICATIONS

N/A.

BACKGROUND

Background and Relevant Art

The brain and various tissues communicate information to various organs, cell clusters, cells, other body parts, and combinations thereof, using electrical signals. Elements of the electrical signal determine the details of the message. For example, each organ, cell cluster, cell, or other body part has a specific targeting frequency and different tissue responses have different response frequencies. Furthermore, some organs may communicate within the organ using electrical signals having specific target and response frequencies. By changing the frequency of the electrical signal, the brain may change the cells targeted by the electrical signal and/or the instructions for the targeted cells.

Childbirth is traumatic on a woman's body. Recovery after childbirth is extensive, and may include contraction of the uterus, stopping bleeding and bruising of the uterus, vagina, perineum, and other areas, repair to the abdominal wall, repair to the uterus, and more. Recovery after vaginal childbirth may involve healing and other recovery of different organs and cell groups than recovery after a caesarean section (C-section). For example, a C-section involves cutting through the abdominal wall and into the uterus. Therefore, recovery after a C-section involves healing the incision into the abdomen and the uterus.

BRIEF SUMMARY

In some embodiments, a method for post-birth recovery includes applying an electromagnetic (EM) field emitter of a pulsed electromagnetic field (PEMF) device to an abdomen of a patient. An initiating signal may be received, and the PEMF device may perform a recovery cycle. Performing the recovery cycle may include setting a plurality of frequency combinations for a plurality of EM fields. Each frequency combination includes a response frequency, a target frequency, and an associated frequency combination period. The plurality of frequency combinations include a stop bleeding response frequency (18 Hz) having a stop bleeding frequency combination period of at least 193 minutes; a remove anesthesia response frequency (19 Hz) having a remove anesthesia frequency combination period of at least one minute; a lidocaine removal response frequency (7 Hz) having a lidocaine removal frequency combination period of at least one minute; a decrease inflammation response frequency (40 Hz) having a decrease inflammation frequency combination period of at least one minute; a repair torn and broken tissue response frequency (124 Hz) having a torn and broken frequency combination period of at least two minutes; a repair trauma response frequency (294 Hz) having a repair trauma frequency combination period of at least one minute; a paralysis mitigation response frequency (321 Hz) having a paralysis mitigation frequency combination period of at least one minute; a reduce allergies response frequency (9 Hz) having a reduce allergies frequency combination period of at least one minute; a reduce pain response frequency (20 Hz) having a reduce pain frequency combination period of at least one minute; an emotional component response frequency (970 Hz) having an emotional component frequency combination period of at least four minutes; a relieve pain and stress response frequency (174 Hz) having a relieve pain and stress frequency combination period of at least two minutes; and a repair DNA response frequency (528 Hz) having a repair DNA frequency combination period of at least two minutes. The method may further include applying the plurality of EM fields using the frequency combination for the associated frequency combination period. In some embodiments, applying the EM field may occur with an EM field device.

This summary is provided to introduce a selection of concepts that are further described below in the detailed description. This summary is not intended to identify key or essential features of the claimed subject matter, nor is it intended to be used as an aid in limiting the scope of the claimed subject matter.

Additional features and advantages of embodiments of the disclosure will be set forth in the description which follows, and in part will be obvious from the description, or may be learned by the practice of such embodiments. The features and advantages of such embodiments may be realized and obtained by means of the instruments and combinations particularly pointed out in the appended claims. These and other features will become more fully apparent from the following description and appended claims, or may be learned by the practice of such embodiments as set forth hereinafter.

BRIEF DESCRIPTION OF THE DRAWINGS

In order to describe the manner in which the above-recited and other features of the disclosure can be obtained, a more particular description will be rendered by reference to specific implementations thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example implementations, the implementations will be described and explained with additional specificity and detail through the use of the accompanying drawings in which.

DETAILED DESCRIPTION

This disclosure generally relates to devices, systems, and methods for post-birth recovery. After childbirth, a patient may receive a pulsed electromagnetic field (PEMF) device. The PEMF device may include one or more electromagnetic (EM) field emitters. The patient may place the EM field emitters on her abdomen and/or back. The PEMF device may cause the EM field emitters to apply an EM field to the patient's abdomen. By applying a target frequency and a response frequency, the EM field emitters may stimulate or induce a tissue healing response in a target group of cells. The PEMF device may cycle through frequency pairings to change the targeted group of cells and/or the healing response. Stimulating various healing responses on various groups of cells and/or organs may improve post-birth recovery.

According to embodiments of the present disclosure, and as will be discussed herein, a first EM field having a target frequency may be applied to a patient's abdomen. The target frequency may be configured to target a specified organ or group of cells. A second EM field having a response frequency may be applied to the patient's abdomen. The response frequency may be configured to stimulate a healing response from the organ or the group of cells. Applying the EM fields with the target frequency and the response frequency to the patient's abdomen may induce a tissue healing response from the organ or the group of cells, thereby improving post-birth recovery.

Figure 1:
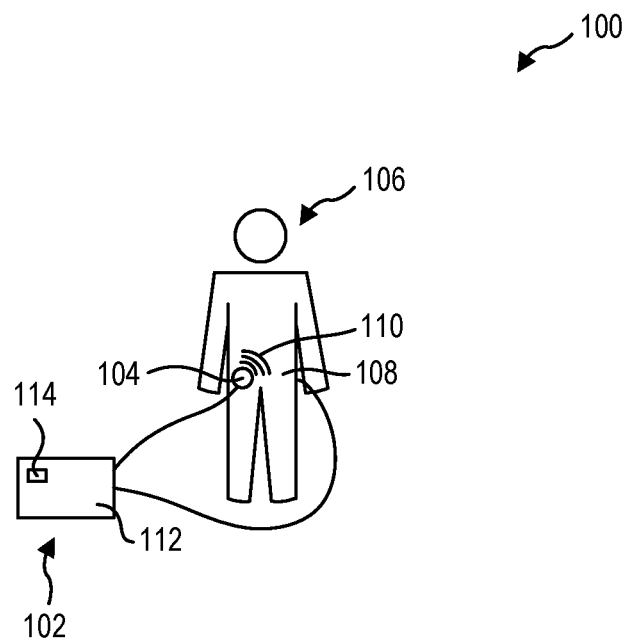
FIG. 1 is a representation of a system for post-birth recovery, according to at least one embodiment of the present disclosure.

Referring now to the figures, FIG. 1 is a representation of a system 100 for post-birth recovery, according to at least one embodiment of the present disclosure. The system 100 includes a pulsed electromagnetic field (PEMF) device 102. The PEMF device 102 may include one or more electromagnetic (EM) field emitters 104. The EM field emitters 104 may be placed on a patient 106. The EM field emitters 104 may be placed on any portion of the patient's 106 body. For example, in the embodiment shown, the EM field emitters 104 may be placed on the abdomen 108 of the patient 106. In some embodiments, the EM field emitters 104 may be placed on any other portion of the patient's 106 body. For example, the EM field emitters 104 may be placed on the patient's back, chest, arms, legs, joints, or any other portion of the patient's 106 body.

In some embodiments, the EM field emitters 104 may be placed close to a target area, a target organ, a target group of cells, and combinations thereof. For the purposes of this disclosure, organs, groups of cells, areas, and so forth will be discussed collectively as organs, including specific examples thereof. However, it should be understood that the term "organ" may encompass any single cell, group of cells, organ, group of organs, parts of organs, and combinations thereof. For example, the term organ may represent the uterus, the cervix, the vagina, the endometrium, the skin, the abdominal wall, blood vessels (e.g., arteries, capillaries, veins), the bladder, the liver, nerves, the nervous system, the solar nerve plexus, the spinal cord, the dura, cerebrospinal fluid (CSF), the medulla, the muscular system, ligaments, connective tissue, fascia, the stomach, the large intestine, the small intestine, endometrium, the genitourinary system, the anterior pituitary system, the immune system, the genitourinary system, the lymphatic system, the oviduct, the ovaries, the ureter, the skin, any other organ, cell, group of cells, and combinations thereof.

During childbirth, various organs and groups of cells in the abdomen 108 may experience trauma and/or need to revert to a pre-birth condition and/or location. In some embodiments, to facilitate post-birth recovery, the EM field emitters 104 may be placed over the abdomen 108 of the patient 106. In this manner, an EM field 110 emitted by the EM field emitter 104 may be received by the organs and groups of cells.

In some embodiments, the EM field emitters 104 may be placed within a placement distance of the target organ. In some embodiments, the placement distance may be in a range having an upper value, a lower value, or upper and lower values including any of less than 1 cm, 1 cm, 2 cm 4 cm, 6 cm, 8 cm, 10 cm, 15 cm, 20 cm, 25 cm, 30 cm, or any value therebetween. For example, the placement distance may be less than 30 cm. In some examples, the placement distance may be greater than 30 cm. In some embodiments, it may be critical that the placement distance is less than 10 cm to allow the EM field 110 to reach the target organ.

In some embodiments, each EM field emitter 104 may apply the EM field 110 with an EM field strength in Gauss (G). In some embodiments, the EM field strength may be a combined EM field strength of the combined EM fields emitted by the EM field emitter 104. In some embodiments, the EM field strength may be in a range having an upper value, a lower value, or upper and lower values including any of 0.1 G, 0.2 G, 0.3 G, 0.4 G, 0.5 G, 0.6 G, 0.7 G, 0.8 G, 0.9 G, 1.0 G, 1.5 G, 2.0 G, 3 G, 4 G, 5 G, 6 G, 8 G, 10 G, or any value therebetween. For example, the EM field strength may be greater than 0.1 G. In another example, the EM field strength may be less than 10.0 G. In yet other examples, the EM field strength may be any value in a range between 0.1 G and 10.0. In some embodiments, it may be critical that the EM field strength is greater than 0.5 G to induce a recovery response in the target organ.

The PEMF device 102 includes a PEMF controller 112. The PEMF controller 112 may control the frequency of an EM field 110 transmitted by the EM field emitters 104. In some embodiments, the PEMF controller 112 may control a duration of transmission of a specific EM frequency. When the EM field emitter 104 emits an EM field 110, the EM field 110 may overlap, encounter, engage, or otherwise contact the body and/or a portion of the body of the patient 106. The EM field 110 may induce an electric current in the patient's 106 body. The frequency of the electric current may be the same as the frequency of the emitted EM field 110. Thus, in some embodiments, the PEMF controller 112 may control the frequency of an induced electrical current in the patient 106.

To communicate with a target organ, the brain uses a target frequency. The brain may then use a response frequency to induce, elicit, or otherwise get a tissue response from the target organ. In other words, cells perform different actions or functions in response to different electrical signals. To both target a target organ and to induce a tissue recovery response from the target organ, the PEMF controller 112 may cause the EM field emitters 104 to emit both a target frequency and a response frequency. Thus, the PEMF device 102 may be a multi-channel PEMF device 102.

In some embodiments, a tissue recovery response may be any response performed by an organ. In some embodiments, the tissue recovery response may be a response by an organ that facilitates recovery from childbirth. For example, tissue recovery responses may include reducing an allergic response, mitigating a concussion, decreasing inflammation, removing lidocaine, reducing pain, mitigating paralysis, relieving pain and stress, removing anesthesia, repairing DNA, regulating secretions, stopping bleeding, repairing torn and broken tissues, repair trauma response, improving vitality, emotional components, and combinations thereof.

In some embodiments, each EM field emitter 104 may have multiple channels. In other words, each EM field emitter 104 may simultaneously (e.g., at the same time) emit multiple EM fields 110. In some embodiments, the EM field emitter 104 may simultaneously apply 1 2, 3, 4, 5, 6, 7, 8, 9, 10, or more EM fields 110. Thus, a single EM field emitter 104 may emit EM fields 110 having both the target frequency and the response frequency. In some embodiments, a single EM field emitter 104 may emit multiple EM fields 110 having multiple target and/or response frequencies. This may help ensure that both the EM fields 110 having the target frequency and the response frequency reach the target organ. In some embodiments, as discussed herein, different EM field emitters 104 may emit EM fields 110 having the same frequency. This may further help to ensure that the EM fields 110 having the target frequency and the response frequency reach the target organ.

In some embodiments, different EM field emitters 104 may emit EM fields 110 having different combinations of target and response frequencies. This may reduce the time that the EM fields 110 are applied to the patient 106. In some embodiments, the different EM fields 110 may have the same target frequency (e.g., target the same organ) and different response frequencies (e.g., induce different responses). In this manner, the PEMF device 102 may induce different responses in the same target organ. In some embodiments, the different EM fields 110 may have the same response frequencies (e.g., induce the same response) and different target frequencies (e.g., target different organs). In this manner, the PEMF device 102 may induce the same response in different target organs. In some embodiments, the different EM fields 110 may have different target frequencies and different response frequencies. In this manner, the PEMF device may induce different tissue healing responses in different target organs, the same tissue healing response in different target organs, or different tissue healing responses in the same target organs. This may allow a medical practitioner to design a recovery cycle that improves post-birth recovery by encouraging tissue healing responses in organs affected by pregnancy and birth.

In some embodiments, each EM field emitter 104 may emit different EM fields 110. For example, a first EM field emitter 104 may emit an EM field 110 having the target frequency, and a second EM field emitter 104 may emit an EM field 110 having the response frequency. This may help increase the strength of the respective EM fields 110, thereby helping the EM fields 110 reach the target organ.

In some embodiments, the PEMF device 102 may have 1, 2, 3, 4, 5, 6, 7, 8, 9, 10, or more channels. In some embodiments, each EM field emitter 104 may have 1 2, 3, 4, 5, 6, 7, 8, 9, 10, or more channels.

In some embodiments, two EM field emitters 104 may be applied to the patient. The EM field emitters 104 may be placed in different locations. For example, a first EM field emitter 104 may be placed on the abdomen 108 of the patient 106 and a second EM field emitter 104 may be placed on the back of the patient 106. In some embodiments, the EM field emitters 104 may be placed such that the respective EM fields 110 may at least partially overlap. In this manner, the EM field 110 may be sure to reach the target organ, thereby improving the strength of the EM signal received by the target organ. In embodiments, the EM field emitters 104 may be placed such that the respective EM fields 110 do not overlap. In this manner, the EM field 110 may contact or cover more target organs or a larger portion of the target organ.

In some embodiments, the EM field emitters 104 may be fixedly attached to the patient 106. For example, in some embodiments, the EM field emitters 104 may be held in place using cloth, gauze, bandages, tape, or other means of securing the EM field emitters 104 to the patient 106. In some embodiments, the PEMF device 102 may be portable. In other words, in some embodiments, the PEMF device 102 may be carried by the patient 106 while performing a recovery cycle (e.g., while the EM field emitters 104 are generating an EM field 110). In this manner, the patient 106 may get up and move around while the PEMF device 102 performs the recovery cycle.

Conventionally, the cells of organs may be induced to perform functions by directly applying an electric current to the patient's body. The electric field may be applied through an electric patch, through a wet cloth with an attached electrode, or any other manner of directly applying an electric current to the patient's body. However, to ensure that the electric current is applied to the correct location, the patch and/or the electrode are placed by a physician or other trained professional. The patient may then stay in the same position for the duration of the therapy. This may be expensive and time-consuming.

In some embodiments, the PEMF device 102 may include a single-button operation. In other words, the PEMF device 102 may come pre-loaded with a recovery cycle, including specific frequencies to be applied, frequency combinations, and frequency application durations. The patient 106 may simply apply the EM field emitters 104, press a start button 114, and the PEMF device 102 may cause the EM field emitters 104 to apply EM fields 110 according to the pre-programed recovery cycle without any additional input, from the patient or otherwise. In this manner, the patient 106 may be able to experience PEMF therapy without the constant attendance of a medical professional. Similarly, the patient 106 may be able to apply the EM fields 110 by herself or apply the EM fields 110 without a medical professional. This may decrease the cost of treatment and increase flexibility in how the treatment is administered to the patient.

Figure 2:
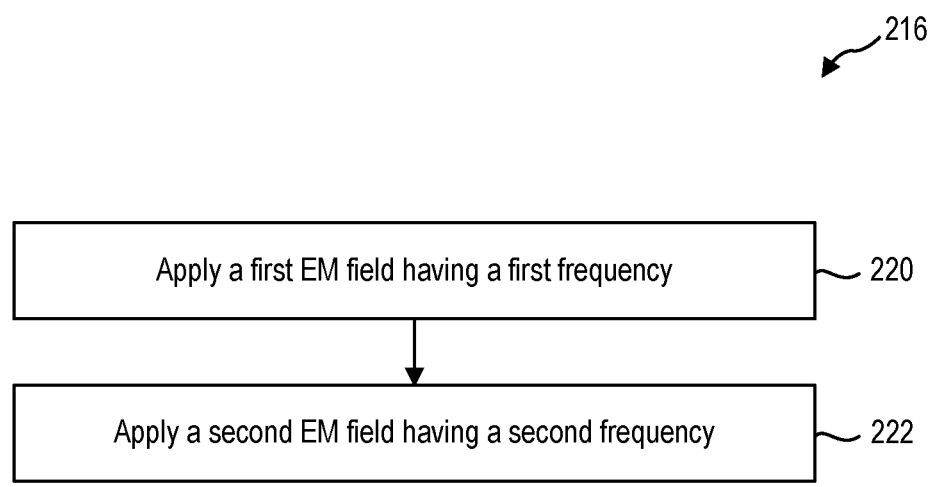
FIG. 2 is a representation of a method for post-birth recovery, according to at least one embodiment of the present disclosure.

FIG. 2 is a representation of a method 216 for post-birth recovery, according to at least one embodiment of the present disclosure. The method 216 may be performed or executed by the PEMF device 102 shown in FIG. 1. Specifically, the PEMF controller 112 may cause the EM field emitters 104 to emit EM fields 110 in accordance with the method 216.

The method 216 may include applying a second EM field having a second frequency at 222. In some embodiments, the second frequency may be a target frequency. In some embodiments, the second frequency may be a response frequency. In some embodiments, if the first frequency is a target frequency, then the second frequency is a response frequency.

In some embodiments, the first EM field and the second EM field may be applied simultaneously. In some embodiments, the first EM field and the second EM field may be applied sequentially. For example, the first EM field having the target frequency may be applied first, and the second EM field having the response frequency may be applied second, and then the order repeated.

In some embodiments, the method 216 may begin when the patient initializes the method 216. For example, the patient may press a single button on the PEMF device or the PEMF controller, and the method 216 may begin without additional input (e.g., no other buttons or other input from the patient into the PEMF device). A first EM field is applied to the patient having a first frequency at 220. In some embodiments, the first frequency may be a target frequency. In some examples, the first frequency is a recovery frequency.

As discussed herein, in some embodiments, the target frequency may be associated with a target organ. Following is a list of target organs and their associated target frequencies (in Hertz (Hz)): anterior pituitary gland target frequency (310 Hz), arteries target frequency (62 Hz), bladder target frequency (37 Hz), capillaries target frequency (162 Hz), connective tissue target frequency (77 Hz), cerebrospinal fluid (CSF) target frequency (288 Hz), dura target frequency (443 Hz), endometrium target frequency (155 Hz), external genitalia target frequency (12 Hz), clitoris target frequency (72 Hz), cervix target frequency (2 Hz), vagina target frequency (19 Hz), bladder sphincter target frequency (178 Hz), urethra target frequency (51 Hz), anus target frequency (61 Hz and/or 74 Hz), rectum target frequency (88 Hz), mucous membranes target frequency (132 Hz), mucous membranes target frequency (243 Hz), tendons target frequency (191 Hz), hemorrhoids (65 Hz), fascia target frequency (152 Hz), genitourinary system target frequency (48 Hz), immune system target frequency (116 Hz), large intestine target frequency (85 Hz), ligaments target frequency (100 Hz), liver target frequency (35 Hz), lymphatic system target frequency (13 Hz), medulla target frequency (94 Hz), muscle system target frequency (46 Hz), nerve target frequency (396 Hz), nervous system target frequency (45 Hz), ovaries target frequency (7 Hz), oviduct target frequency (4 Hz), pineal gland target frequency (102 Hz), skin target frequency (355 Hz), small intestine target frequency (22 Hz), solar nerve plexus target frequency (200 Hz), spinal cord target frequency (10 Hz), stomach target frequency (32 Hz), sympathetic nervous system target frequency (562 Hz), ureter target frequency (60 Hz), uterus target frequency (34 Hz), veins target frequency (79 Hz), and whole body target frequency (0.1 and/or 1 Hz). In some embodiments, one or more frequencies and/or frequency pairs may be homeopathic and/or naturopathic, such as balancing energy centers (35 Hz and/or 102 Hz), hypoxia (880 Hz and/or 7.4 Hz), constitutional factors (38 Hz and/or 6.8 Hz), an emotional component (970 Hz), restore joy (33 Hz).

As discussed herein, in some embodiments, the tissue or organ response may be associated with a response frequency. Following is a list of tissue responses and their associated response frequencies (in Hz): reduce allergies response frequency (9 Hz), reduce concussion response frequency (94 Hz), decrease inflammation response frequency (40 Hz), emotional component response frequency (970 Hz), lidocaine removal response frequency (7 Hz), reduce pain response frequency (20 Hz), paralysis mitigation response frequency (321 Hz), relieve pain and stress response frequency (174 Hz), remove anesthesia response frequency (19 Hz), repair DNA response frequency (528 Hz), regulate secretions response frequency (81 Hz), stop bleeding response frequency (18 Hz), repair torn and broken tissue response frequency (124 Hz), repair trauma response frequency (294 Hz), and improve vitality response frequency (49 Hz). In some embodiments, one or more response frequencies may be associated with an emotional component (970 Hz). In some embodiments, under Chinese medicine, certain organs may be associated with different emotional responses, including the heart (33 Hz) which holds joy, the kidney (23 Hz), transverse colon (27 Hz), gallbladder (38 Hz), bladder (37 Hz), skin (355 Hz), and the spleen and lymphatic system (13 Hz).

In some embodiments, the tolerance of the target frequency and/or the response frequency may be within plus or minus 0.3 Hz. In some embodiments, the tolerance of the target frequency and/or the response frequency may be within plus or minus 0.2 Hz. Each person's body is unique, and may respond to slightly (e.g., within the tolerance) different target and/or response frequencies. In some embodiments, to ensure that a patient's body induces the desired responses at the desired response, a recovery cycle may use different wave shapes, modulations, or other modifications to the waveform to cover the frequency and the tolerance range.

In some embodiments, a frequency combination may be the specific combination of frequencies that induce a specific response at a target organ. In other words, the frequency combination may be the combination of a first EM field having a response frequency and a second EM field having a target frequency. The frequency combination may further be associated with a frequency combination period.

According to embodiments of the present disclosure, the frequency combination and the associated frequency combination period (e.g., the application period specific to a given combination of EM field frequencies) is critical to post-birth recovery. Mothers have been recovering from childbirth for millennia. Nevertheless, recovery from childbirth is still a long process, and is physically, mentally, and emotionally challenging. A long post-birth recovery may result in a reduced quality of care of a child. Extensive research and experimentation have attempted to improve post-birth recovery, such as through faster healing and/or reduced pain. Conventional post-birth recovery mechanisms include waiting for the body to heal itself and managing pain and/or symptoms using medications. However, medication may have adverse side effects. Therefore, there has been a long-felt need to improve the post-birth recovery process.

The inventors of the present disclosure have determined that the frequency combinations and their associated frequency combination periods may improve post-birth recovery. Specifically, the frequency combinations and associated frequency combination periods disclosed herein provide an improvement in many aspects of post-birth recovery, including pain reduction, pain management, anesthesia recovery, bleeding reduction, emotional recovery, energy levels, other improvements, and combinations thereof.

In some embodiments, the first EM field and/or the second EM field may be applied for a frequency combination period. In some embodiments, the frequency combination period may be in a range having an upper value, a lower value, or upper and lower values including any of 15 seconds, 30 seconds, 1 minute, 2 minutes, 3 minutes, 4 minutes, 5 minutes, 6 minutes, 7 minutes, 8 minutes, 9 minutes, 10 minutes, 15 minutes, 20 minutes, 25 minutes, 30 minutes, 60 minutes, 120 minutes, 180 minutes, 240 minutes, or any value therebetween. For example, the frequency combination period may be greater than 15 seconds. In another example, the frequency combination period may be less than 240 minutes. In yet other examples, the frequency combination period may be any value in a range between 15 seconds and 240 minutes. In some embodiments, it may be critical that the frequency combination period is non-zero and less than 15 minutes to induce a healing response from the target organ. In some embodiments, it may be critical that the frequency combination is greater than 1 minute to induce a healing response from the target organ. In some embodiments, the frequency combination period may be less than 15 seconds or more than 240 minutes.

In some embodiments, the frequency combination periods disclosed herein may be a minimum frequency combination period. For example, the frequency combination periods disclosed herein may be the shortest amount of time for which a frequency or frequency combination is applied to the patient to achieve the desired response. In some embodiments, a longer frequency combination period may see an improved response, a marginally improved response, or no change in response. In some embodiments, the frequency combination periods disclosed herein may be a maximum frequency combination period. For example, the frequency combination periods disclosed herein may be the longest amount of time for which a frequency or frequency combination is applied to the patient to achieve the desired response. In some embodiments, a longer frequency combination period may see a reduced response, a marginally reduced response, or no change in response.

In some embodiments, specific tissue responses induced by the response frequency may generally have the same frequency combination period. For example, a reduce allergies response frequency (9 Hz) may have generally have a reduce allergies frequency combination period of at least one minute for each target organ. A concussion reduction response frequency (94 Hz) may generally have a concussion reduction frequency combination period of at least two minutes for each target organ. A decrease inflammation response (40 Hz) may generally have a decrease inflammation frequency combination period of at least four minutes for each target organ. An emotional component response (970 Hz) may generally have an emotional component frequency combination period of at least four minutes for each target organ. A lidocaine removal response (7 Hz) may generally have a lidocaine removal frequency combination period of at least one minute. A reduce pain response (20 Hz) may generally have a reduce pain frequency combination period of between one and four minutes, or at least four minutes. A paralysis mitigation response (321 Hz) may generally have a paralysis mitigation frequency combination period of at least one minute. A relieve pain and stress response (174 Hz) may generally have a relieve pain and stress frequency combination period of at least two minutes. A remove anesthesia response (19 Hz) may generally have a remove anesthesia frequency combination period of at least one minute. A repair DNA response (528 Hz) may generally have a repair DNA frequency combination period of at least one minutes. A secretion regulation response (81 Hz) may generally have a secretion regulation frequency combination period of at least two or at least six minutes. A stop bleeding response (18 Hz) may generally have a stop bleeding frequency combination period of at least 193 minutes. A repair torn and broken tissue response (124 Hz) may generally have a repair torn and broken tissue frequency combination period of at least two minutes, at least four minutes, at least six minutes, or at least 10 minutes. A repair trauma response (294 Hz) may generally have a repair trauma frequency combination period of at least one minute. An increase vitality response (49 Hz) may generally have an increase vitality frequency combination period of at least one minute.

The inventors of the present disclosure have found that the general frequency combination periods disclosed herein for the tissue response frequencies will significantly improve post-birth recovery. For example, the inventors found that the frequency combination period for the repair torn and broken tissue response (124 Hz) of at least two minutes may improve healing of tissue torn, broken, or otherwise damaged during childbirth. As discussed further herein, in combination with other specific frequency combinations and frequency combination periods, this may significantly improve post-birth recovery.

In some embodiments, the first EM field and the second EM field may be applied for the same frequency combination period. In some embodiments, the first EM field and the second EM field may be applied for different frequency combination periods. For example, the first EM field may have a response frequency and the second EM field may have a target frequency, and a healing cycle may change the target frequency of the second EM field without changing the response frequency of the first EM field. In some examples, the response frequency may be changed without changing the target frequency.

Cesarean-Section Post-Birth Recovery

In accordance with embodiments of the present disclosure, frequency combinations disclosed herein may be beneficial to assist a mother in recovering from a Cesarean-section birth. While the specific frequency combinations disclosed below may be directed to recovering from a Cesarean-section surgery, it should be understood that the frequency combinations disclosed herein may be interchangeably used to recover from a vaginal birth as well.

According to embodiments of the present disclosure, frequency combinations disclosed herein having an associated minimum frequency combination period may include: stop bleeding response (18 Hz), arteries target (62 Hz), and 193 minute frequency combination period; stop bleeding response (18 Hz), capillaries target (162 Hz), and at least 193 minute frequency combination period, remove anesthesia response (19 Hz), nervous system target (45 Hz), and at least 1 minute frequency combination period; remove anesthesia response (19 Hz), liver target (35 Hz), and at least one minute frequency combination period; remove anesthesia response (19 Hz), fascia target (142 Hz), and at least one minute frequency combination period; remove anesthesia response (19 Hz), nerve target (396 Hz), and at least one minute frequency combination period; lidocaine removal response (7 Hz), nerve target (396 Hz), and at least one minute frequency combination period; lidocaine removal response (7 Hz), CSF target (288 Hz), and at least one minute frequency combination period; lidocaine removal response (7 Hz), spinal cord target (10 Hz), and at least one minute frequency combination period; decrease inflammation response (40 Hz), skin target (355 Hz), and at least four minute frequency combination period; decrease inflammation response (40 Hz), immune system target (116 Hz), and at least four minute frequency combination period; decrease inflammation response (40 Hz), artery target (62 Hz), and at least four minute frequency combination period; decrease inflammation response (40 Hz), uterus target (34 Hz), and at least four minute frequency combination period; decrease inflammation response (40 Hz), stomach target (32 Hz), and at least four minute frequency combination period; decrease inflammation response (40 Hz), connective tissue target (77 Hz), and at least four minute frequency combination period; decrease inflammation response (40 Hz), muscle system target (46 Hz), and at least four minute frequency combination period; decrease inflammation response (40 Hz), ureter target (60 Hz), and at least four minute frequency combination period; decrease inflammation response (40 Hz), oviduct target (4 Hz), and at least four minute frequency combination period; decrease inflammation response (40 Hz), fascia target (142 Hz), and at least four minute frequency combination period; decrease inflammation response (40 Hz), lymphatic system target (13 Hz), and at least four minute frequency combination period; decrease inflammation response (40 Hz), nerve target (396 Hz), and at least four minute frequency combination period; decrease inflammation response (40 Hz), spinal cord target (10 Hz), and at least four minute frequency combination period; decrease inflammation response (40 Hz), bladder target (37 Hz), and at least four minute frequency combination period; decrease inflammation response (40 Hz), large intestine target (85 Hz), and at least four minute frequency combination period; decrease inflammation response (40 Hz), small intestine target (22 Hz), and at least four minute frequency combination period; decrease inflammation response (40 Hz), ligaments target (100 Hz), and at least four minute frequency combination period; decrease inflammation response (40 Hz), endometrium target (155 Hz), and at least four minute frequency combination period; decrease inflammation response (40 Hz), genitourinary system target (48 Hz), and at least four minute frequency combination period; decrease inflammation response (40 Hz), nervous system target (45 Hz), and at least four minute frequency combination period; decrease inflammation response (40 Hz), veins target (79 Hz), and at least four minute frequency combination period.

In some embodiments, the frequency combinations may include: repair torn and broken tissue response (124 Hz), skin target (355 Hz), and at least four minute frequency combination period; repair torn and broken tissue response (124 Hz), immune system target (116 Hz), and at least two minute frequency combination period; repair torn and broken tissue response (124 Hz), artery target (62 Hz), and at least two minute frequency combination period; repair torn and broken tissue response (124 Hz), uterus target (62 Hz), and at least four minute frequency combination period; repair torn and broken tissue response (124 Hz), stomach target (32 Hz), and at least four minute frequency combination period; repair torn and broken tissue response (124 Hz), connective tissue target (77 Hz), and at least six minute frequency combination period; repair torn and broken tissue response (124 Hz), muscle system target (46 Hz), and at least four minute frequency combination period; repair torn and broken tissue response (124 Hz), ureter target (60 Hz), and at least four minute frequency combination period; repair torn and broken tissue response (124 Hz), oviduct target (4 Hz), and at least four minute frequency combination period; repair torn and broken tissue response (124 Hz), fascia target (142 Hz), and at least 10 minute frequency combination period; repair torn and broken tissue response (124 Hz), lymphatic system target (13 Hz), and at least four minute frequency combination period; repair torn and broken tissue response (124 Hz), nerve target (396 Hz), and at least four minute frequency combination period; repair torn and broken tissue response (124 Hz), spinal cord target (10 Hz), and at least four minute frequency combination period; repair torn and broken tissue response (124 Hz), bladder target (37 Hz), and at least four minute frequency combination period; repair torn and broken tissue response (124 Hz), large intestine target (85 Hz), and at least four minute frequency combination period; repair torn and broken tissue response (124 Hz), small intestine target (4 Hz), and at least four minute frequency combination period; repair torn and broken tissue response (124 Hz), ligaments target (100 Hz), and at least six minute frequency combination period; repair torn and broken tissue response (124 Hz), endometrium target (155 Hz), and at least four minute frequency combination period; repair torn and broken tissue response (124 Hz), genitourinary system target (48 Hz), and at least four minute frequency combination period; repair torn and broken tissue response (124 Hz), veins target (79 Hz), and at least four-minute frequency combination period; repair torn and broken tissue response (124 Hz), ovaries target (7 Hz), and at least four-minute frequency combination period.

In some embodiments, emotional response frequencies may pair with organs that are known to harbor those feelings through tradition Chinese medicine. For example, in some embodiments, the frequency combinations may include: balance energy centers response (102 Hz), heart target (33 Hz); repair trauma response (294 Hz), skin target (355 Hz), and at least one minute frequency combination period; repair trauma response (294 Hz), immune system target (116 Hz), and at least one minute frequency combination period; repair trauma response (294 Hz), artery target (62 Hz), and at least one minute frequency combination period; repair trauma response (294 Hz), uterus target (62 Hz), and at least one minute frequency combination period; repair trauma response (294 Hz), stomach target (32 Hz), and at least one minute frequency combination period; repair trauma response (294 Hz), stomach target (32 Hz), and at least one minute frequency combination period; repair trauma response (294 Hz), connective tissue target (77 Hz), and at least one minute frequency combination period; repair trauma response (294 Hz), muscle system target (46 Hz), and at least one minute frequency combination period; repair trauma response (294 Hz), muscle system target (46 Hz), and at least one minute frequency combination period; repair trauma response (294 Hz), ureter target (60 Hz), and at least one minute frequency combination period; repair trauma response (294 Hz), oviduct target (4 Hz), and at least one minute frequency combination period; repair trauma response (294 Hz), fascia target (142 Hz), and at least one minute frequency combination period; repair trauma response (294 Hz), lymphatic system target (13 Hz), and at least one minute frequency combination period; repair trauma response (294 Hz), nerve target (396 Hz), and at least one minute frequency combination period; repair trauma response (294 Hz), spinal cord target (10 Hz), and at least one minute frequency combination period; repair trauma response (294 Hz), bladder target (37 Hz), and at least one minute frequency combination period; repair trauma response (294 Hz), large intestine target (85 Hz), and at least one minute frequency combination period; repair trauma response (294 Hz), small intestine target (4 Hz), and at least one minute frequency combination period; repair trauma response (294 Hz), ligaments target (100 Hz), and at least one minute frequency combination period; repair trauma response (294 Hz), endometrium target (155 Hz), and at least one minute frequency combination period; repair trauma response (294 Hz), genitourinary system target (48 Hz), and at least one minute frequency combination period; repair trauma response (294 Hz), nervous system target (45 Hz), and at least one minute frequency combination period; repair trauma response (294 Hz), veins target (79 Hz), and at least one minute frequency combination period; repair trauma response (294 Hz), ovaries target (7 Hz), and at least one minute frequency combination period.

In some embodiments, the frequency combination may include paralysis mitigation response (321 Hz), skin target (355 Hz), and at least one minute frequency combination period; and at least one minute frequency combination period; paralysis mitigation response (321 Hz), immune system target (116 Hz), and at least one minute frequency combination period; paralysis mitigation response (321 Hz), artery target (62 Hz) and at least one minute frequency combination period; paralysis mitigation response (321 Hz), uterus target (62 Hz), and at least one minute frequency combination period; paralysis mitigation response (321 Hz), stomach target (32 Hz), and at least one minute frequency combination period; paralysis mitigation response (321 Hz), connective tissue target (77 Hz), and at least one minute frequency combination period; paralysis mitigation response (321 Hz), muscle system target (46 Hz), and at least one minute frequency combination period; paralysis mitigation response (321 Hz), ureter target (60 Hz), and at least one minute frequency combination period; paralysis mitigation response (321 Hz), oviduct target (4 Hz), and at least one minute frequency combination period; paralysis mitigation response (321 Hz), fascia target (142 Hz), and at least one minute frequency combination period; paralysis mitigation response (321 Hz), lymphatic system target (13 Hz), and at least one minute frequency combination period; paralysis mitigation response (321 Hz), nerve target (396 Hz), and at least one minute frequency combination period; paralysis mitigation response (321 Hz), spinal cord target (10 Hz), and at least one minute frequency combination period; paralysis mitigation response (321 Hz), bladder target (37 Hz), and at least one minute frequency combination period; paralysis mitigation response (321 Hz), large intestine target (85 Hz), and at least one minute frequency combination period; paralysis mitigation response (321 Hz), small intestine target (4 Hz), and at least one minute frequency combination period; paralysis mitigation response (321 Hz), ligaments target (100 Hz), and at least one minute frequency combination period; paralysis mitigation response (321 Hz), endometrium target (155 Hz), and at least one minute frequency combination period; paralysis mitigation response (321 Hz), genitourinary system target (48 Hz), and at least one minute frequency combination period; paralysis mitigation response (321 Hz), nervous system target (45 Hz), and at least one minute frequency combination period; paralysis mitigation response (321 Hz), veins target (79 Hz), and at least one minute frequency combination period.

In some embodiments, the frequency combination may include reduce allergies response (9 Hz), skin target (355 Hz), and at least one minute frequency combination period; reduce allergies response (9 Hz), immune system target (116 Hz), and at least one minute frequency combination period; reduce allergies response (9 Hz), artery target (62 Hz), and at least one minute frequency combination period; reduce allergies response (9 Hz), uterus target (62 Hz), and at least one minute frequency combination period; reduce allergies response (9 Hz), stomach target (32 Hz), and at least one minute frequency combination period; reduce allergies response (9 Hz), connective tissue target (77 Hz), and at least one minute frequency combination period; reduce allergies response (9 Hz), muscle system target (46 Hz), and at least one minute frequency combination period; reduce allergies response (9 Hz), ureter target (60 Hz), and at least one minute frequency combination period; reduce allergies response (9 Hz), oviduct target (4 Hz), and at least one minute frequency combination period; reduce allergies response (9 Hz), fascia target (142 Hz), and at least one minute frequency combination period; reduce allergies response (9 Hz), lymphatic system target (13 Hz), and at least one minute frequency combination period; reduce allergies response (9 Hz), nerve target (396 Hz), and at least one minute frequency combination period; reduce allergies response (9 Hz), spinal cord target (10 Hz), and at least one minute frequency combination period; reduce allergies response (9 Hz), bladder target (37 Hz), and at least one minute frequency combination period; reduce allergies response (9 Hz), large intestine target (85 Hz), and at least one minute frequency combination period; reduce allergies response (9 Hz), small intestine target (4 Hz), and at least one minute frequency combination period; reduce allergies response (9 Hz), ligaments target (100 Hz), and at least one minute frequency combination period; reduce allergies response (9 Hz), endometrium target (155 Hz), and at least one minute frequency combination period; reduce allergies response (9 Hz), genitourinary system target (48 Hz), and at least one minute frequency combination period; reduce allergies response (9 Hz), nervous system target (45 Hz), and at least one minute frequency combination period.

In some embodiments, the frequency combination may include: decrease inflammation response (40 Hz), dura target (443 Hz), and at least four minute frequency combination period; repair torn and broken tissue response (124 Hz), dura target (443 Hz), and at least four minute frequency combination period; paralysis mitigation response (321 Hz), dura target (443 Hz), and at least one minute frequency combination period; repair trauma response (294 Hz), dura target (443 Hz), and at least one minute frequency combination period; reduce pain response (20 Hz), dura target (443 Hz), and at least one minute frequency combination period; reduce pain response (20 Hz), skin target (355 Hz), and at least four minute frequency combination period; reduce pain response (20 Hz), immune system target (116 Hz), and at least one minute frequency combination period; reduce pain response (20 Hz), artery target (62 Hz), and at least four minute frequency combination period; reduce pain response (20 Hz), uterus target (34 Hz), and at least four minute frequency combination period; reduce pain response (20 Hz), stomach target (32 Hz), and at least two minute frequency combination period; reduce pain response (20 Hz), connective tissue target (77 Hz), and at least four minute frequency combination period; reduce pain response (20 Hz), muscle system target (46 Hz), and at least four minute frequency combination period; reduce pain response (20 Hz), ureter target (60 Hz), and at least four minute frequency combination period; reduce pain response (20 Hz), oviduct target (4 Hz), and at least one minute frequency combination period; reduce pain response (20 Hz), fascia target (142 Hz), and at least four minute frequency combination period; reduce pain response (20 Hz), lymphatic system target (13 Hz), and at least four minute frequency combination period; reduce pain response (20 Hz), nerve target (396 Hz), and at least four minute frequency combination period; reduce pain response (20 Hz), spinal cord target (10 Hz), and at least two minute frequency combination period; reduce pain response (20 Hz), bladder target (37 Hz), and at least two minute frequency combination period; reduce pain response (20 Hz), large intestine target (85 Hz), and at least four minute frequency combination period; reduce pain response (20 Hz), small intestine target (22 Hz), and at least two minute frequency combination period; reduce pain response (20 Hz), ligaments target (100 Hz), and at least four minute frequency combination period; reduce pain response (20 Hz), endometrium target (155 Hz), and at least four minute frequency combination period; reduce pain response (20 Hz), genitourinary system target (48 Hz), and at least four minute frequency combination period; reduce pain response (20 Hz), ovaries target (7 Hz), and at least four minute frequency combination period; reduce pain response (20 Hz), veins target (79 Hz), and at least four minute frequency combination period.

In some embodiments, the frequency combination may include: emotional component response (970 Hz), skin target (355 Hz), and at least one minute frequency combination period; emotional component response (970 Hz), immune system target (116 Hz), and at least one minute frequency combination period; emotional component response (970 Hz), artery target (62 Hz), and at least one minute frequency combination period; emotional component response (970 Hz), uterus target (34 Hz), and at least one minute frequency combination period; emotional component response (970 Hz), stomach target (32 Hz), and at least one minute frequency combination period; emotional component response (970 Hz), connective tissue target (77 Hz), and at least one minute frequency combination period; emotional component response (970 Hz), muscle system target (46 Hz), and at least one minute frequency combination period; emotional component response (970 Hz), ureter target (60 Hz), and at least one minute frequency combination period; emotional component response (970 Hz), oviduct target (4 Hz), and at least one minute frequency combination period; emotional component response (970 Hz), fascia target (142 Hz), and at least one minute frequency combination period; emotional component response (970 Hz), lymphatic system target (13 Hz), and at least one minute frequency combination period; emotional component response (970 Hz), nerve target (396 Hz), and at least one minute frequency combination period; emotional component response (970 Hz), spinal cord target (10 Hz), and at least one minute frequency combination period; emotional component response (970 Hz), bladder target (37 Hz), and at least one minute frequency combination period; emotional component response (970 Hz), large intestine target (85 Hz), and at least one minute frequency combination period; emotional component response (970 Hz), small intestine target (22 Hz), and at least one minute frequency combination period; emotional component response (970 Hz), ligaments target (100 Hz), and at least one minute frequency combination period; emotional component response (970 Hz), endometrium target (155 Hz), and at least one minute frequency combination period; emotional component response (970 Hz), genitourinary system target (48 Hz), and at least one minute frequency combination period; emotional component response (970 Hz), veins target (79 Hz), and at least one minute frequency combination period.

In some embodiments, the frequency combination may include: relieve pain and stress response (174 Hz), skin target (355 Hz), and at least one minute frequency combination period; relieve pain and stress response (174 Hz), immune system target (116 Hz), and at least one minute frequency combination period; relieve pain and stress response (174 Hz), artery target (62 Hz), and at least one minute frequency combination period; relieve pain and stress response (174 Hz), uterus target (34 Hz), and at least one minute frequency combination period; relieve pain and stress response (174 Hz), stomach target (32 Hz), and at least one minute frequency combination period; relieve pain and stress response (174 Hz), connective tissue target (77 Hz), and at least one minute frequency combination period; relieve pain and stress response (174 Hz), muscle system target (46 Hz), and at least one minute frequency combination period; relieve pain and stress response (174 Hz), ureter target (60 Hz), and at least one minute frequency combination period; relieve pain and stress response (174 Hz), oviduct target (4 Hz), and at least one minute frequency combination period; relieve pain and stress response (174 Hz), fascia target (142 Hz), and at least one minute frequency combination period; relieve pain and stress response (174 Hz), lymphatic system target (13 Hz), and at least one minute frequency combination period; relieve pain and stress response (174 Hz), nerve target (396 Hz), and at least one minute frequency combination period; relieve pain and stress response (174 Hz), spinal cord target (10 Hz), and at least one minute frequency combination period; relieve pain and stress response (174 Hz), bladder target (37 Hz), and at least one minute frequency combination period; relieve pain and stress response (174 Hz), large intestine target (85 Hz), and at least one minute frequency combination period; relieve pain and stress response (174 Hz), small intestine target (22 Hz), and at least one minute frequency combination period; relieve pain and stress response (174 Hz), ligaments target (100 Hz), and at least one minute frequency combination period; relieve pain and stress response (174 Hz), endometrium target (155 Hz), and at least one minute frequency combination period; relieve pain and stress response (174 Hz), genitourinary system target (48 Hz), and at least one minute frequency combination period; relieve pain and stress response (174 Hz), veins target (79 Hz), and at least one minute frequency combination period.

In some embodiments, the frequency combination may include: repair DNA response (528 Hz), skin target (355 Hz), and at least two minute frequency combination period; repair DNA response (528 Hz), immune system target (116 Hz), and at least two minute frequency combination period; repair DNA response (528 Hz), artery target (62 Hz), and at least two minute frequency combination period; repair DNA response (528 Hz), uterus target (34 Hz), and at least two minute frequency combination period; repair DNA response (528 Hz), stomach target (32 Hz), and at least two minute frequency combination period; repair DNA response (528 Hz), connective tissue target (77 Hz), and at least two minute frequency combination period; repair DNA response (528 Hz), muscle system target (46 Hz), and at least two minute frequency combination period; repair DNA response (528 Hz), ureter target (60 Hz), and at least two minute frequency combination period; repair DNA response (528 Hz), oviduct target (4 Hz), and at least two minute frequency combination period; repair DNA response (528 Hz), fascia target (142 Hz), and at least two minute frequency combination period; repair DNA response (528 Hz), lymphatic system target (13 Hz), and at least two minute frequency combination period; repair DNA response (528 Hz), nerve target (396 Hz), and at least two minute frequency combination period; repair DNA response (528 Hz), spinal cord target (10 Hz), and at least two minute frequency combination period; repair DNA response (528 Hz), bladder target (37 Hz), and at least two minute frequency combination period; repair DNA response (528 Hz), large intestine target (85 Hz), and at least two minute frequency combination period; repair DNA response (528 Hz), small intestine target (22 Hz), and at least two minute frequency combination period; repair DNA response (528 Hz), ligaments target (100 Hz), and at least two minute frequency combination period; repair DNA response (528 Hz), endometrium target (155 Hz), and at least two minute frequency combination period; repair DNA response (528 Hz), genitourinary system target (48 Hz), and at least two minute frequency combination period; repair DNA response (528 Hz), nervous system target (79 Hz), and at least two minute frequency combination period.

In some embodiments, the frequency combination may include: an emotional component response (970 Hz), a restore joy target (33 Hz), and at least three minute frequency combination period; a secretion regulation response (81 Hz), a fascia target (142 Hz), and at least six minute frequency combination period; a vitality improvement response (49 Hz), a fascia target (142 Hz), and at least two minute frequency combination period; a paralysis mitigation response (321 Hz), a whole body target (1 Hz), and at least one minute frequency combination period; a concussion reduction response (94 Hz), a solar nerve plexus target (200 Hz), and at least two minute frequency combination period; an emotional component response (970 Hz), a solar nerve plexus target (200 Hz), and at least two minute frequency combination period; a concussion reduction response (94 Hz), a medulla target (94 Hz), and at least two minute frequency combination period; a paralysis mitigation response (321 Hz), a medulla target (94 Hz), and at least two minute frequency combination period; an reduce allergies response (9 Hz), a medulla target (94 Hz), and at least two minute frequency combination period; a vitality improvement response (49 Hz), a medulla target (94 Hz), and at least one minute frequency combination period; a concussion reduction response (94 Hz), an anterior pituitary gland target (310 Hz), and at least two minute frequency combination period; a paralysis mitigation response (321 Hz), an anterior pituitary gland target (310 Hz), and at least two minute frequency combination period; a secretion regulation response (81 Hz), an anterior pituitary gland target (310 Hz), and at least two minute frequency combination period; a vitality improvement response (49 Hz), an anterior pituitary gland target (310 Hz), and at least one minute frequency combination period.

In some embodiments, emotional response frequencies may pair with organs that are known to harbor those feelings through tradition Chinese medicine. In some embodiments, the frequency combination may include: constitutional factors response and target (6.8 Hz and 38 Hz), and at least two minute frequency combination period; a vitality improvement response and target (49 Hz and 0.1 Hz), and at least one minute frequency combination period; a balance energy centers response and target (35 Hz and 102 Hz), and at least one minute frequency combination period; an emotional component response (970 Hz), a whole body target (1 Hz), and at least one minute frequency combination period; a vitality improvement response (49 Hz), a whole body target (1 Hz), and at least one minute frequency combination period; a concussion reduction response (94 Hz), a solar nerve plexus target (200 Hz), and at least one minute frequency combination period; an emotional component response (970 Hz), a solar nerve plexus target (200 Hz), and at least one minute frequency combination period; a decrease inflammation response (40 Hz), a nervous system target (45 Hz), and at least one minute frequency combination period; a decrease inflammation response (40 Hz), a sympathetic nervous system target (562 Hz), and at least two minute frequency combination period; an emotional component response (970 Hz), a sympathetic nervous system target (562 Hz), and at least one minute frequency combination period; an emotional component response (970 Hz), a fear, terror, and defensiveness target (e.g., transverse colon, 27 Hz) transverse colon, and at least two minute frequency combination period; an emotional component response (970 Hz), a fear and fixed ideas target (e.g., kidney, 23 Hz), and at least one minute frequency combination period; an emotional component response (970 Hz), an anger and aggression target (e.g., liver, 35 Hz), and at least one minute frequency combination period; an emotional component response (970 Hz), a guild and resentment target (e.g., gall bladder, 38 Hz), and at least one minute frequency combination period; an emotional component response (970 Hz), a hurt feelings target (e.g., bladder 37 Hz), and at least one minute frequency combination period; an emotional component response (970 Hz), a worry and oversensitivity target (e.g., spleen and lymphatics, 13 Hz), and at least one minute frequency combination period; an emotional component response (970 Hz), a shame target (e.g., skin, 355 Hz), and at least one minute frequency combination period; an emotional component response (970 Hz), a restore joy target (e.g., heart, 33 Hz), and at least one minute frequency combination period; an emotional component response (970 Hz), a pineal target (102 Hz), and at least one minute frequency combination period; and a balance energy centers response and target (35 Hz and 102 Hz), and at least one minute frequency combination period.

According to embodiments of the present disclosure, the frequency combinations and frequency combination periods discussed above may include any combination of response frequency and target frequency not disclosed herein. Furthermore, the frequency combination periods may include any frequency combination period not explicitly disclosed. For example, a frequency combination having a frequency combination period of at least four minutes may be modified to include a frequency combination period of less than four minutes.

Vaginal Birth Post-Birth Recovery

In accordance with embodiments of the present disclosure, frequency combinations disclosed herein may be beneficial to assist a mother in recovering from a vaginal (e.g., a "natural") birth. While the specific frequency combinations disclosed below may be directed to recovering from a vaginal birth, it should be understood that the frequency combinations disclosed herein may be interchangeably used to recover from a Cesarean-section surgery as well.

In some embodiments, the frequency combination may include: a stop bleeding response (18 Hz), an endometrium target (155 Hz), and at least four minute frequency combination period; a decrease inflammation response (40 Hz), an external genitalia target (12 Hz), and at least four minute frequency combination period; a decrease inflammation response (40 Hz), a clitoris target (72 Hz), and at least four minute frequency combination period; a decrease inflammation response (40 Hz), a cervix target (2 Hz), and at least four minute frequency combination period; a decrease inflammation response (40 Hz), a vagina target (19 Hz), and at least four minute frequency combination period; a decrease inflammation response (40 Hz), a bladder sphincter target (178 Hz), and at least four minute frequency combination period; a decrease inflammation response (40 Hz), a urethra target (51 Hz), and at least four minute frequency combination period; a decrease inflammation response (40 Hz), an anus target (61 Hz), and at least four minute frequency combination period; a decrease inflammation response (40 Hz), an anus target (74 Hz), and at least four minute frequency combination period; a decrease inflammation response (40 Hz), a rectum target (88 Hz), and at least four minute frequency combination period; a decrease inflammation response (40 Hz), a mucous membrane target (132 Hz), and at least four minute frequency combination period; a decrease inflammation response (40 Hz), a mucous membrane target (243 Hz), and at least four minute frequency combination period; a decrease inflammation response (40 Hz), a muscles and shoulders target (76 Hz), a decrease inflammation response (40 Hz), a tendons target (191 Hz), and at least four minute frequency combination period.

In some embodiments, the frequency combination may include: a reduce allergies response (9 Hz), an external genitalia target (12 Hz), and at least one minute frequency combination period; a reduce allergies response (9 Hz), a clitoris target (72 Hz), and at least one minute frequency combination period; a reduce allergies response (9 Hz), a cervix target (2 Hz), and at least one minute frequency combination period; a reduce allergies response (9 Hz), a vagina target (19 Hz), and at least one minute frequency combination period; a bladder sphincter target (178 Hz), and at least one minute frequency combination period; a reduce allergies response (9 Hz), a urethra target (51 Hz), and at least one minute frequency combination period; at least one minute frequency combination period; an anus target (61 Hz), and at least one minute frequency combination period; a reduce allergies response (9 Hz), an anus target (74 Hz), and at least one minute frequency combination period; a reduce allergies response (9 Hz), a rectum target (88 Hz), and at least one minute frequency combination period; a reduce allergies response (9 Hz), a mucous membrane target (132 Hz), and at least one minute frequency combination period; a reduce allergies response (9 Hz), a mucous membrane target (243 Hz), and at least one minute frequency combination period; a reduce allergies response (9 Hz), a muscles and shoulders target (76 Hz), and at least one minute frequency combination period; a reduce allergies response (9 Hz), a tendons target (191 Hz).

In some embodiments, the frequency combination may include: a repair trauma response (294 Hz), an external genitalia target (12 Hz), and at least one minute frequency combination period; a repair trauma response (294 Hz), a clitoris target (72 Hz), and at least one minute frequency combination period; a repair trauma response (294 Hz), and at least one minute frequency combination period; a repair trauma response (294 Hz), a vagina target (19 Hz), and at least one minute frequency combination period; a repair trauma response (294 Hz), a bladder sphincter target (178 Hz), and at least one minute frequency combination period; a repair trauma response (294 Hz), a urethra target (51 Hz), and at least one minute frequency combination period; a repair trauma response (294 Hz), an anus target (61 Hz), and at least one minute frequency combination period; a repair trauma response (294 Hz), an anus target (74 Hz), and at least one minute frequency combination period; a repair trauma response (294 Hz), and at least one minute frequency combination period; a repair trauma response (294 Hz), a mucous membrane target (132 Hz), and at least one minute frequency combination period; a mucous membrane target (243 Hz), a repair trauma response (294 Hz), a muscles and shoulders target (76 Hz), and at least one minute frequency combination period; a repair trauma response (294 Hz), a tendons target (191 Hz), and at least one minute frequency combination period.

In some embodiments, the frequency combination may include: a paralysis mitigation response (321 Hz), an external genitalia target (12 Hz), and at least one minute frequency combination period; a paralysis mitigation response (321 Hz), a clitoris target (72 Hz), and at least one minute frequency combination period; a paralysis mitigation response (321 Hz), a cervix target (2 Hz), and at least one minute frequency combination period; a paralysis mitigation response (321 Hz), a vagina target (19 Hz), and at least one minute frequency combination period; a paralysis mitigation response (321 Hz), a bladder sphincter target (178 Hz), a paralysis mitigation response (321 Hz), a urethra target (51 Hz), and at least one minute frequency combination period; a paralysis mitigation response (321 Hz), an anus target (61 Hz), and at least one minute frequency combination period; a paralysis mitigation response (321 Hz), an anus target (74 Hz), and at least one minute frequency combination period; a paralysis mitigation response (321 Hz), a rectum target (88 Hz), and at least one minute frequency combination period; a paralysis mitigation response (321 Hz), a mucous membrane target (132 Hz), and at least one minute frequency combination period; a paralysis mitigation response (321 Hz), a mucous membrane target (243 Hz), and at least one minute frequency combination period; a paralysis mitigation response (321 Hz), a muscles and shoulders target (76 Hz), a paralysis mitigation response (321 Hz), a tendons target (191 Hz), and at least one minute frequency combination period.

In some embodiments, the frequency combination may include: a repair torn and broken tissue response (124 Hz), an external genitalia target (12 Hz), and at least four minute frequency combination period; a repair torn and broken tissue response (124 Hz), a clitoris target (72 Hz), and at least four minute frequency combination period; a repair torn and broken tissue response (124 Hz), a vagina target (19 Hz), and at least four minute frequency combination period; a repair torn and broken tissue response (124 Hz), a bladder sphincter target (178 Hz), and at least four minute frequency combination period; a repair torn and broken tissue response (124 Hz), and at least two minute frequency combination period; a repair torn and broken tissue response (124 Hz), and at least two minute frequency combination period; a repair torn and broken tissue response (124 Hz), an anus target (61 Hz), and at least two minute frequency combination period; a repair torn and broken tissue response (124 Hz), an anus target (74 Hz), and at least two minute frequency combination period; a repair torn and broken tissue response (124 Hz), a rectum target (88 Hz), and at least two minute frequency combination period; a mucous membrane target (132 Hz), and at least four minute frequency combination period; a repair torn and broken tissue response (124 Hz), a mucous membrane target (243 Hz), and at least four minute frequency combination period; a repair torn and broken tissue response (124 Hz), a muscles and shoulders target (76 Hz), and at least four minute frequency combination period; a repair torn and broken tissue response (124 Hz), a tendons target (191 Hz), and at least four minute frequency combination period.

In some embodiments, the frequency combination may include: an emotional component response (970 Hz), an external genitalia target (12 Hz), and at least three minute frequency combination period; an emotional component response (970 Hz), a clitoris target (72 Hz), and at least three minute frequency combination period; an emotional component response (970 Hz), a cervix target (2 Hz), an emotional component response (970 Hz), and at least three minute frequency combination period; an emotional component response (970 Hz), a vagina target (19 Hz), and at least three minute frequency combination period; an emotional component response (970 Hz), a bladder sphincter target (178 Hz), and at least three minute frequency combination period; an emotional component response (970 Hz), a urethra target (51 Hz), and at least three minute frequency combination period; an emotional component response (970 Hz), an anus target (61 Hz), and at least three minute frequency combination period; an anus target (74 Hz), and at least three minute frequency combination period; an emotional component response (970 Hz), a rectum target (88 Hz), and at least three minute frequency combination period; an emotional component response (970 Hz), a mucous membrane target (132 Hz), and at least three minute frequency combination period; an emotional component response (970 Hz), a mucous membrane target (243 Hz), and at least three minute frequency combination period; an emotional component response (970 Hz), a muscles and shoulders target (76 Hz), and at least three minute frequency combination period; an emotional component response (970 Hz), and at least three minute frequency combination period.

In some embodiments, the frequency combination may include: a repair DNA response (528 Hz), an external genitalia target (12 Hz), and at least four minute frequency combination period; a clitoris target (72 Hz), and at least four minute frequency combination period; a repair DNA response (528 Hz), a cervix target (2 Hz), and at least four minute frequency combination period; a repair DNA response (528 Hz), a vagina target (19 Hz), and at least four minute frequency combination period; a repair DNA response (528 Hz), a bladder sphincter target (178 Hz), and at least four minute frequency combination period; a repair DNA response (528 Hz), a urethra target (51 Hz), and at least four minute frequency combination period; a repair DNA response (528 Hz), an anus target (61 Hz), and at least four minute frequency combination period; a repair DNA response (528 Hz), an anus target (74 Hz), and at least four minute frequency combination period; a repair DNA response (528 Hz), a rectum target (88 Hz), a repair DNA response (528 Hz), a mucous membrane target (132 Hz), and at least four minute frequency combination period; a repair DNA response (528 Hz), and at least four minute frequency combination period; a repair DNA response (528 Hz), a muscles and shoulders target (76 Hz), and at least four minute frequency combination period; a repair DNA response (528 Hz), a tendons target (191 Hz), and at least four minute frequency combination period.

In some embodiments, the frequency combination may include: a relieve pain and stress response (174 Hz), an external genitalia target (12 Hz), and at least four minute frequency combination period; a clitoris target (72 Hz), and at least four minute frequency combination period; a relieve pain and stress response (174 Hz), a cervix target (2 Hz), and at least four minute frequency combination period; a relieve pain and stress response (174 Hz), a vagina target (19 Hz), a bladder sphincter target (178 Hz), and at least four minute frequency combination period; a relieve pain and stress response (174 Hz), a urethra target (51 Hz), and at least four minute frequency combination period; a relieve pain and stress response (174 Hz), an anus target (61 Hz), a relieve pain and stress response (174 Hz), and at least four minute frequency combination period; a relieve pain and stress response (174 Hz), and at least four minute frequency combination period; a relieve pain and stress response (174 Hz), a mucous membrane target (132 Hz), and at least four minute frequency combination period; a relieve pain and stress response (174 Hz), a mucous membrane target (243 Hz), and at least four minute frequency combination period; a relieve pain and stress response (174 Hz), a muscles and shoulders target (76 Hz), a relieve pain and stress response (174 Hz), a tendons target (191 Hz), and at least four minute frequency combination period.

In some embodiments, the frequency combination may include: a reduce pain response (20 Hz), an external genitalia target (12 Hz), and at least four minute frequency combination period; a reduce pain response (20 Hz), a clitoris target (72 Hz), and at least four minute frequency combination period; a reduce pain response (20 Hz), a cervix target (2 Hz), and at least four minute frequency combination period; a reduce pain response (20 Hz), a vagina target (19 Hz), and at least four minute frequency combination period; a reduce pain response (20 Hz), a bladder sphincter target (178 Hz), and at least four minute frequency combination period; a reduce pain response (20 Hz), a urethra target (51 Hz), and at least four minute frequency combination period; a reduce pain response (20 Hz), an anus target (61 Hz), and at least four minute frequency combination period; a reduce pain response (20 Hz), an anus target (74 Hz), and at least four minute frequency combination period; a reduce pain response (20 Hz), a rectum target (88 Hz), and at least four minute frequency combination period; a reduce pain response (20 Hz), a mucous membrane target (132 Hz), and at least four minute frequency combination period; a reduce pain response (20 Hz), a mucous membrane target (243 Hz), and at least four minute frequency combination period; a reduce pain response (20 Hz), a muscles and shoulders target (76 Hz), and at least four minute frequency combination period; a reduce pain response (20 Hz), a tendons target (191 Hz), and at least four minute frequency combination period.

In some embodiments, the frequency combination may include: a repair torn and broken tissue response (124 Hz), a rectum target (88 Hz), and at least five minute frequency combination period; a repair torn and broken tissue response (124 Hz), a hemorrhoids target (65 Hz), and at least five minute frequency combination period; a reduce inflammation response (40 Hz), a rectum target (88 Hz), and at least five minute frequency combination period; a reduce inflammation response (40 Hz), a hemorrhoids target (65 Hz), and at least five minute frequency combination period; a vitality improvement response (49 Hz), a rectum target (88 Hz), and at least five minute frequency combination period; a vitality improvement response (49 Hz), a hemorrhoids target (65 Hz), and at least five minute frequency combination period; a stop bleeding response (18 Hz), a rectum target (88 Hz), and at least five minute frequency combination period; a stop bleeding response (18 Hz), a hemorrhoids target (65 Hz), and at least five minute frequency combination period; a reduce congestion target (50 Hz), a veins target (79 Hz), and at least five minute frequency combination period; a repair torn and broken tissue response (124 Hz), a veins target (79 Hz), and at least five minute frequency combination period; a reduce inflammation response (40 Hz), a veins target (79 Hz), and at least five minute frequency combination period; a vitality improvement response (49 Hz), a veins target (79 Hz), and at least five minute frequency combination period; a stop bleeding response (18 Hz), a veins target (79 Hz), and at least five minute frequency combination period.

According to embodiments of the present disclosure, the frequency combinations and frequency combination periods discussed above may include any combination of response frequency and target frequency not disclosed herein. Furthermore, the frequency combination periods may include any frequency combination period not explicitly disclosed. For example, a frequency combination having a frequency combination period of at least four minutes may be modified to include a frequency combination period of less than four minutes.

Figure 3:
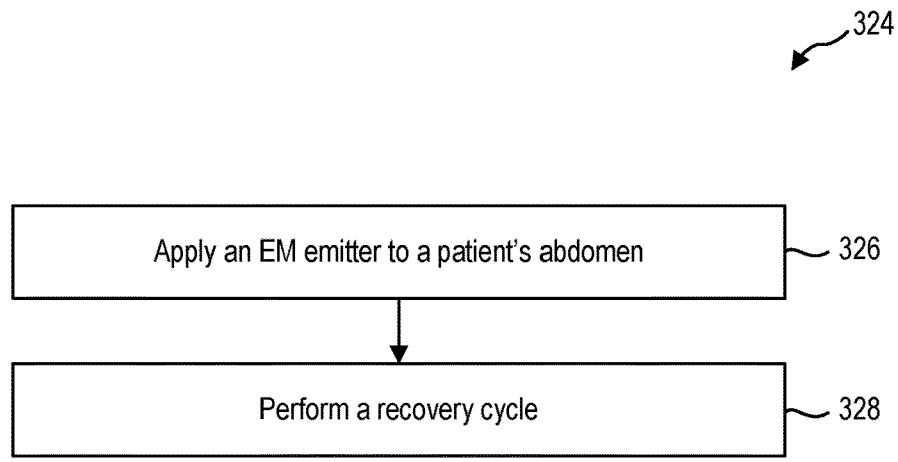
FIG. 3 is a representation of another method for post-birth recovery, according to at least one embodiment of the present disclosure.

FIG. 3 is a representation of a method 324 for post-birth recovery, according to at least one embodiment of the present disclosure. In accordance with embodiments of the present disclosure, the method 324 may be performed or executed by the PEMF device 102 shown in FIG. 1. Specifically, the PEMF controller 112 may cause the EM field emitters 104 to emit EM fields 110 in accordance with the method 324.

The method 324 may include applying an EM field emitter to the abdomen of a patient at 326. Applying the EM field emitter may include placing the EM field emitter on the patient's abdomen near the target organ or organs. For example, applying the EM field emitter may include placing the EM field emitter on the patient's abdomen within a placement distance of the target organ, as discussed herein. In some embodiments, applying the EM field emitter may include placing a multiple EM field emitters on the patient's abdomen. In some embodiments, applying the EM field emitter may include placing a first EM field emitter on the patient's abdomen and a second EM field emitter on the patient's back or side.

In some embodiments, applying the EM field emitter may include a patient placing the EM field emitter without a health care professional or health care provider. In this manner, the patient may perform the method 324 at home, without the need to go into a doctor's office or to have a health care professional come to her home.

The method 324 may further include performing a recovery cycle at 328. In some embodiments, performing a recovery cycle may include applying EM fields to the patient's abdomen using the EM field emitters placed there in act 326.

Figure 4:
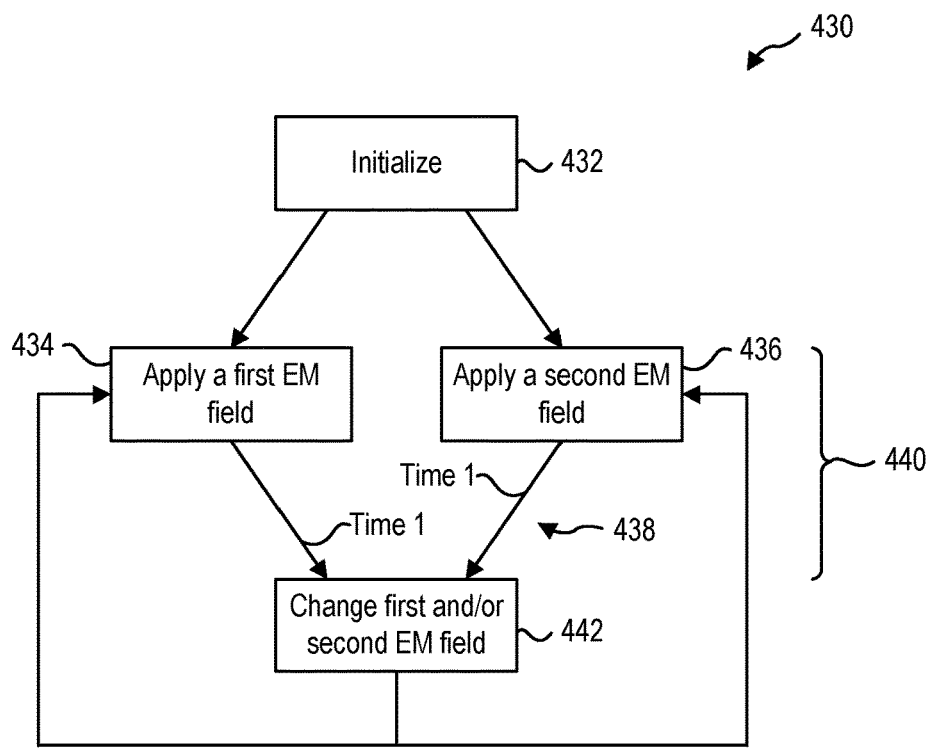
FIG. 4 is a representation of a recovery cycle, according to at least one embodiment of the present disclosure.

FIG. 4 is a representation of a recovery cycle 430, according to at least one embodiment of the present disclosure. The recovery cycle 430 may be performed or executed by the PEMF device 102 shown in FIG. 1. Specifically, the PEMF controller 112 may cause the EM field emitters 104 to emit EM fields 110 in accordance with the recovery cycle 430.

The recovery cycle 430 may begin with a patient-initiated initialization at 432. The initialization may include the patient pressing a button on the PEMF device, initializing the recovery cycle 430 from a computing device, a mobile device, or other remote computing device, utilizing a voice-activated control, any other initialization action, and combinations thereof. This may allow the patient to select when to begin the recovery cycle 430.

The recovery cycle 430 may then apply a first EM field having a first EM frequency at 434. The recovery cycle 430 may further include applying a second EM field having a second EM frequency at 436. In some embodiments, the first EM field and the second EM field may be applied simultaneously, or at the same time. In some embodiments, the first EM field and the second EM field may be applied sequentially.

In some embodiments, the recovery cycle 430 may apply the first EM field and the second EM field for an application period 438. For example, the first EM field and the second EM field may be applied simultaneously, and the both the first EM field and the second EM field may applied for the same application period 438. In some examples, the first EM field and the second EM field may be applied for different application periods 438.

According to embodiments of the present disclosure, the combination of the first EM field having the first EM frequency and the second EM field having the second EM frequency may be a frequency combination 440, and the application period 438 may be the frequency combination period. As discussed with respect to FIG. 2, the frequency combinations 440 may include a response frequency and a response frequency. Thus, the frequency combination 440 may include any of the frequency combinations discussed with respect to FIG. 2. In some embodiments, applying the first EM field and applying the second EM field may be combined into a single act of applying a frequency combination 440.

The recovery cycle 430 may further include changing the first and/or the second EM field at 442. For example, changing the first and/or the second EM field may include changing the frequency of the first and/or the second EM field. This may result in a new frequency combination 440. The new frequency combination 440 may then be applied (e.g., the modified first EM field and the modified second EM field may be applied for a period of time). The recovery cycle 430 may loop through applying frequency combinations 440, modifying frequency combinations, and applying the modified frequency combinations until a pre-determined list of frequency combinations 440 have been applied.

According to embodiments of the present disclosure, the recovery cycle 430 may include a pre-determined arrangement of frequency combinations 440. In other words, the recovery cycle 430 may apply frequency combinations in a specific frequency combination order that is configured to maximize the post-birth recovery of the patient. In some embodiments, the frequency combination order may be the order discussed above with respect to FIG. 2. In some embodiments, the frequency combination order may be any order of any frequency combination discussed herein.

According to embodiments of the present disclosure, the inventors have determined through experimentation that the frequency combinations disclosed herein significantly improve post-birth recovery. Patients of the inventors have reported increased mobility, reduced pain, increased wellness, improved mood, improved happiness, and other recovery benefits, especially compared to previous births by the same patient. These results indicate that the frequency combinations and the frequency combination order improve post-birth recovery in comparison to conventional post-birth recovery techniques.

In some embodiments, the recovery cycle 430 may apply the frequency combinations 440 based on the response frequency. For example, the recovery cycle 430 may apply a group or a set of frequency combinations 440 where the response frequency is kept constant. After the target frequency is changed one or more times, the response frequency may be changed.

In some embodiments, frequency combinations 440 may be applied in a response frequency order. The response frequency order may be the order in which response frequencies are applied. However, it should be understood that a single response frequency may be applied for multiple target frequencies in a row. In some embodiments, the response frequency order may include: stop bleeding response (18 Hz); remove anesthesia response (19 Hz); lidocaine removal response (7 Hz); decrease inflammation response (40 Hz); repair torn and broken tissue response (124 Hz); reduce trauma response (294 Hz); paralysis mitigation response (321 Hz); reduce allergies response (9 Hz); reduce pain response (20 Hz); emotional component response (970 Hz); relieve pain and stress response (174 Hz); and repair DNA response (528 Hz). In some embodiments, the response frequency order may include a stop bleeding response (18 Hz), a reduce inflammation response (40 Hz), a reduce allergies response (9 Hz), a reduce trauma response (294 Hz), a paralysis mitigation response (321 Hz), a repair torn and broken tissue response (124 Hz), an emotional component response (970 Hz), a repair DNA response (528 Hz), a relieve pain and stress response (174 Hz), a reduce pain response (20 Hz), a repair torn and broken tissue response (124 Hz), a reduce inflammation response (40 Hz), an improve vitality response (49 Hz), a stop bleeding response (18 Hz), a reduce congestion response (50 Hz), a repair torn and broken tissue response (124 Hz), a reduce inflammation response (40 Hz), an improve vitality response (40 Hz), and a stop bleeding response (18 Hz). However, it should be understood that embodiments of the present disclosure include any response frequency order disclosed herein. Furthermore, any response frequency may be presented in any order.

In some embodiments, frequency combinations 440 may be applied in a target frequency order. The target frequency order may be the order in which target frequencies are applied. However, it should be understood that a single target frequency may be applied for multiple response frequencies in a row. In some embodiments, the target frequency order may include: skin target (355 Hz); immune system target (116 Hz); artery target (62 Hz); uterus target (34 Hz); stomach target (32 Hz); connective tissue target (77 Hz); muscle system target (46 Hz); ureter target (60 Hz); oviduct target (4 Hz); fascia target (142 Hz); lymphatic system target (13 Hz); nerve target (396 Hz); spinal cord target (10 Hz); bladder target (37 Hz); large intestine target (85 Hz); small intestine target (22 Hz); ligaments target (100 Hz); endometrium target (155 Hz); genitourinary system target (48 Hz); and nervous system target (45 Hz). In some embodiments, the target frequency order may include: an external genitalia target (12 Hz), a clitoris target (72 Hz), a cervix target (2 Hz), a vagina target (19 Hz), a bladder sphincter target (178 Hz), a urethra target (51 Hz), an anus target (61 Hz), an anus target (74 Hz), a rectum target (88 Hz), a mucous membrane target (132 Hz), a mucous membrane target (243 Hz), a muscles and shoulders target (76 Hz), and a tendons target (191 Hz). However, it should be understood that embodiments of the present disclosure include any target frequency order disclosed herein. Furthermore, any target frequency may be presented in any order.

Figure 5:
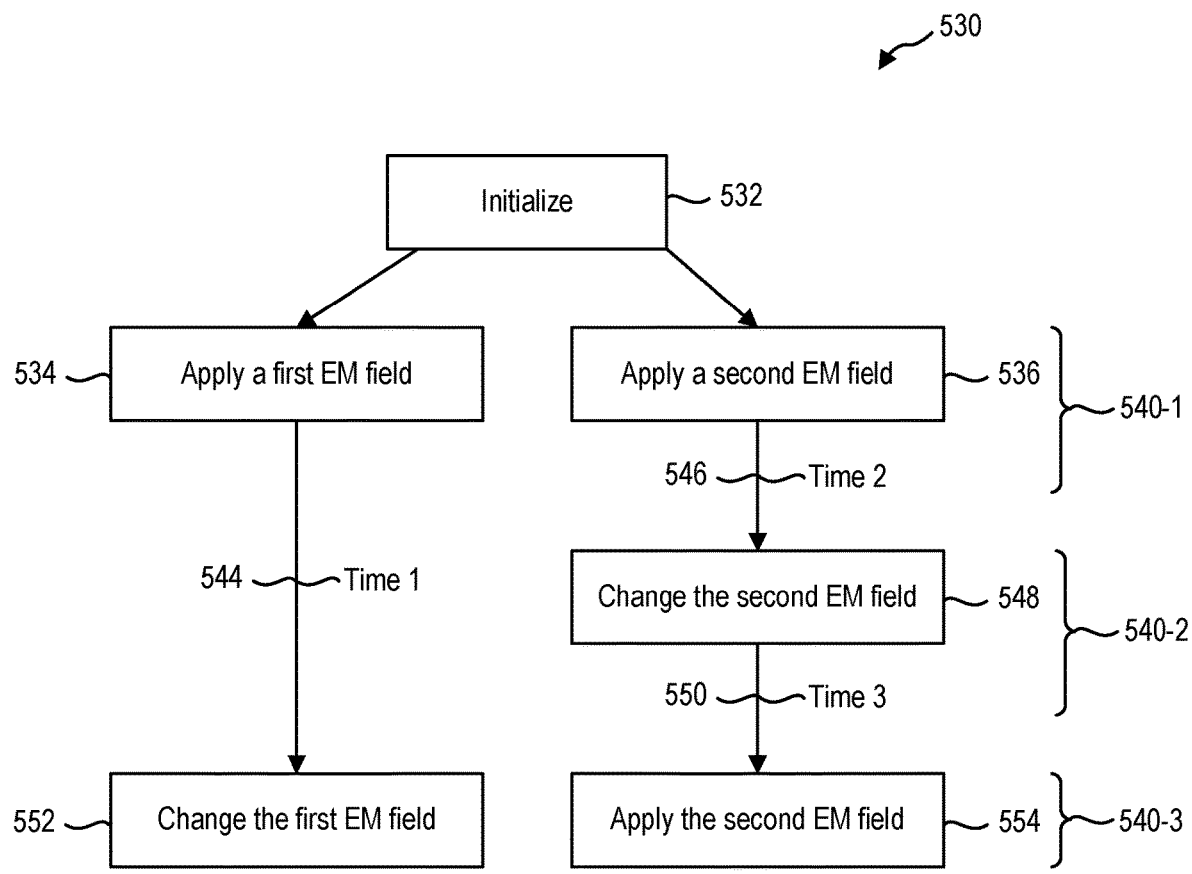
FIG. 5 is a representation of another recovery cycle, according to at least one embodiment of the present disclosure.

FIG. 5 is a representation of a recovery cycle 530, according to at least one embodiment of the present disclosure. The recovery cycle 530 may be performed or executed by the PEMF device 102 shown in FIG. 1. Specifically, the PEMF controller 112 may cause the EM field emitters 104 to emit EM fields 110 in accordance with the recovery cycle 530.

The recovery cycle 530 may be initiated by the patient at 532. In some embodiments, after initialization, the recovery cycle 530 may include applying a first EM field having a first EM frequency at 534 and applying a second EM field having a second EM frequency at 536. The combination of the first EM frequency and the second EM frequency may be a first frequency combination 540-1.

The first EM field may be applied for a first time 544 and the second EM field may be applied for a second time 546. The second time 546 may be less than the first time 544. While the first EM field is being applied, the second EM field may be changed at 548 to have a second frequency. The changed second EM field may be applied for a third time 550. The combination of the first EM field and the changed second EM field may be a second frequency combination 540-2. The first EM field may be maintained through changing the second EM field and while the changed second EM field is being applied. Thus, the first time 544 may be equal to the second time 546 plus the third time 550. In some embodiments, the second EM field may be changed multiple times while the first EM field is maintained.

The recovery cycle 530 may further include changing the first EM field at 552 and applying the second EM field at 554. The second EM field applied at 554 may be the changed second EM field, the original second EM field, or a newly changed second EM field. The changed first EM field and the second EM field may be a third frequency combination 540-3. It should be understood that the first EM field and/or the second EM field may be repeatedly changed until the recovery cycle 530 is completed.

As may be seen in the recovery cycle of FIG. 5, the first EM field and/or the second EM field may be changed simultaneously or together. Similar to the discussion above with respect to FIG. 4, the recovery cycle may repeatedly cycle through a pre-determined set of frequency combinations 540 to promote post-birth recovery.

Figure 6:
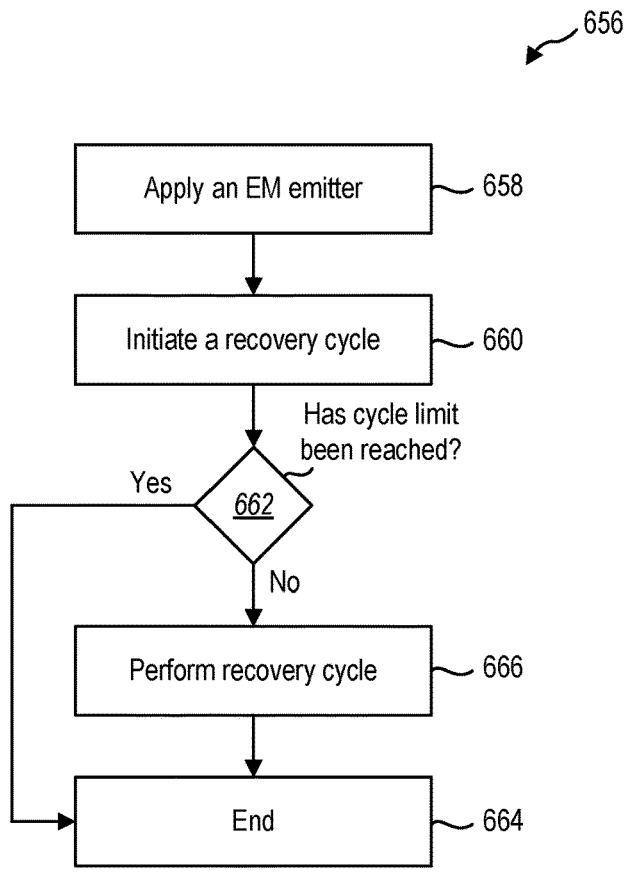
FIG. 6 is a representation of yet another method for post-birth recovery, according to at least one embodiment of the present disclosure.

FIG. 6 is a representation of a method 656 of post-birth recovery, according to at least one embodiment of the present disclosure. The method 656 may be performed or executed by the PEMF device 102 shown in FIG. 1. Specifically, the PEMF controller 112 may cause the EM field emitters 104 to emit EM fields 110 in accordance with the method 656.

The method 656 may include applying an EM field emitter at 658 to the patient's abdomen or other location on the patient's body. The method 636 may further include the patient initiating a recovery cycle at 660. The patient may initiate the recovery cycle using a button or other start mechanism on a PEMF device. In some embodiments, the patient may initiate the recovery cycle at the patient's home, without help or the presence of a medical professional.

When the patient initiates the recovery cycle, the PEMF device may determine whether a cycle limit has been reached at 662. If the cycle limit has been reached, then the method 656 may be over at 664, and the PEMF device may not execute a recovery cycle. If the cycle limit has not been reached, then the PEMF device may execute a recovery cycle, as disclosed herein.

The cycle limit may be a determination of how much that patient has used the PEMF device (e.g., the total use of the PEMF device). For example, the cycle limit may determine a number of recovery cycles performed by the patient. If the patient has performed more than a pre-determined number of recovery cycles, then the cycle limit has been reached. In some embodiments, the pre-determined number of recovery cycles may include 1, 2, 3, 4, 5, 6, 7, 8, 9, 10, or more recovery cycles.

In some examples, the cycle limit may be a total operating time of the PEMF device. If the patient has operated the PEMF device for a total time, regardless of fully or partially completed cycles, that exceeds the cycle limit, then the cycle limit has been reached. In some embodiments, the pre-determined total time may be 1 hour, 2 hour, 4 hours, 6 hours, 8 hours, 10 hours, 12 hours, 18 hours, 24 hours, 36 hours, 48 hours, or any value therebetween.

In some examples, the cycle limit may be a calendar time (e.g., days, weeks, months, years). If the patient tries to operate the PEMF device after a calendar deadline, then the cycle limit has been reached. In some embodiments, the cycle limit may be 1 week after shipping, 2 weeks after purchase/rental, 3 weeks after purchase/rental, 4 weeks after purchase/rental, 6 weeks after purchase/rental, 8 weeks after purchase/rental, 12 weeks after purchase/rental, 16 weeks after purchase/rental, or any value therebetween.

In some embodiments, the patient may not personally own the PEMF device. Because the PEMF device is used in the patient's home (or used by the patient wherever she desires), the patient may be one of several people to use a single PEMF device. To encourage reusability, and prevent theft of PEMF devices, a cycle tracker may be included on the PEMF device that tracks usage of the PEMF device. When the cycle tracker indicates that the PEMF device has exceeded the cycle limit, then the PEMF device may not execute any more recovery cycles until reset by the manufacturer or an administrator. In this manner, a patient may use the PEMF device during recovery and return the PEMF device to the manufacturer and/or administrator.

Figure 7:
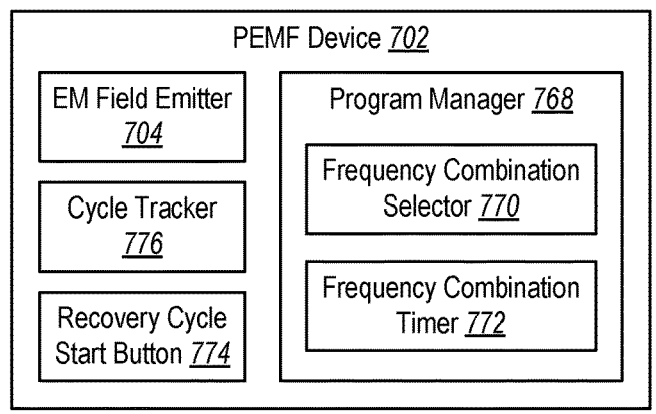
FIG. 7 is a schematic representation of a PEMF device, according to at least one embodiment of the present disclosure.

FIG. 7 is a schematic representation of a PEMF device 702, according to at least one embodiment of the present disclosure. In some embodiments, the PEMF device 702 may include one or more EM field emitters 704. The EM field emitters 704 may be connected to the PEMF device 702 with a wired connection or a wireless connection.

In some embodiments, the PEMF device 702 may include a program manager 768. The program manager 768 may manage the operation of the PEMF device 702, including application of EM fields to the patient through the EM field emitters 704. For example, the program manager 768 may provide instructions to the EM field emitters 704 to generate EM field(s) having a specific frequency combination for a specific frequency combination period.

In some embodiments, the program manager 768 may include a frequency combination selector 770 and a frequency combination timer 772. The program manager 768 may execute a recovery cycle by selecting EM field frequencies with the frequency combination selector 770 and by determining frequency combination periods with the frequency combination timer 772. The program manager 768 may then provide instructions to the EM field emitter 704 to generate the EM fields determined by the frequency combination selector 770 for the durations determined by the frequency combination timer 772.

The PEMF device 702 may further include a recovery cycle start button 774. The recovery cycle start button 774 may be a single interface, interaction, input device, or other input mechanism that the patient may interact with to start a recovery cycle without additional input. In this manner, the patent may begin a recovery cycle without the presence of a medical professional.

The PEMF device 702 may further include a cycle tracker 776. The cycle tracker 776 may track how much the PEMF device 702 has been used (e.g., the total use of the PEMF device). If a patient has exceeded a pre-determined cycle limit, then the cycle tracker 776 may instruct the PEMF device 702 not to execute a recovery cycle.

Figure 8:
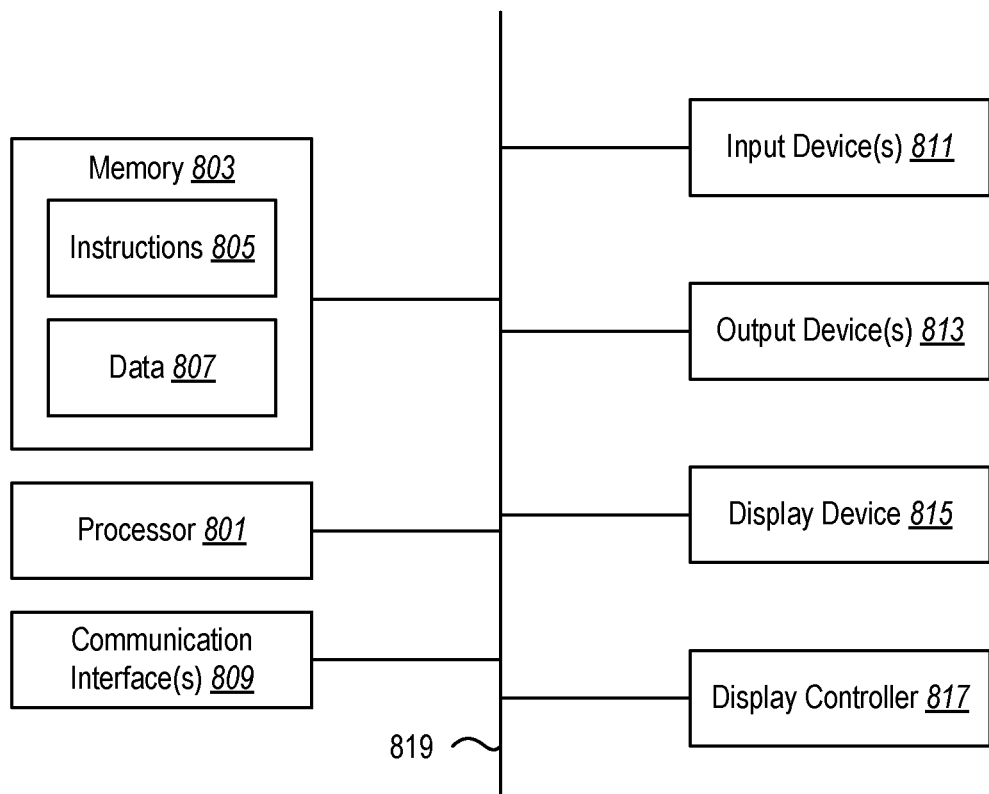
FIG. 8 is a representation of a computing system, according to at least one embodiment of the present disclosure.

FIG. 8 illustrates certain components that may be included within a computer system 819. One or more computer systems 819 may be used to implement the various devices, components, and systems described herein.

The computer system 819 includes a processor 801. The processor 801 may be a general-purpose single or multi-chip microprocessor (e.g., an Advanced RISC (Reduced Instruction Set Computer) Machine (ARM)), a special purpose microprocessor (e.g., a digital signal processor (DSP)), a microcontroller, a programmable gate array, etc. The processor 801 may be referred to as a central processing unit (CPU). Although just a single processor 801 is shown in the computer system 819 of FIG. 8, in an alternative configuration, a combination of processors (e.g., an ARM and DSP) could be used.

The computer system 819 also includes memory 803 in electronic communication with the processor 801. The memory 803 may be any electronic component capable of storing electronic information. For example, the memory 803 may be embodied as random access memory (RAM), read-only memory (ROM), magnetic disk storage media, optical storage media, flash memory devices in RAM, on-board memory included with the processor, erasable programmable read-only memory (EPROM), electrically erasable programmable read-only memory (EEPROM) memory, registers, and so forth, including combinations thereof.

Instructions 805 and data 807 may be stored in the memory 803. The instructions 805 may be executable by the processor 801 to implement some or all of the functionality disclosed herein. Executing the instructions 805 may involve the use of the data 807 that is stored in the memory 803. Any of the various examples of modules and components described herein may be implemented, partially or wholly, as instructions 805 stored in memory 803 and executed by the processor 801. Any of the various examples of data described herein may be among the data 807 that is stored in memory 803 and used during execution of the instructions 805 by the processor 801.

A computer system 819 may also include one or more communication interfaces 809 for communicating with other electronic devices. The communication interface(s) 809 may be based on wired communication technology, wireless communication technology, or both. Some examples of communication interfaces 809 include a Universal Serial Bus (USB), an Ethernet adapter, a wireless adapter that operates in accordance with an Institute of Electrical and Electronics Engineers (IEEE) 802.11 wireless communication protocol, a Bluetooth® wireless communication adapter, and an infrared (IR) communication port.

A computer system 819 may also include one or more input devices 811 and one or more output devices 813. Some examples of input devices 811 include a keyboard, mouse, microphone, remote control device, button, joystick, trackball, touchpad, and lightpen. Some examples of output devices 813 include a speaker and a printer. One specific type of output device that is typically included in a computer system 819 is a display device 815. Display devices 815 used with embodiments disclosed herein may utilize any suitable image projection technology, such as liquid crystal display (LCD), light-emitting diode (LED), gas plasma, electroluminescence, or the like. A display controller 817 may also be provided, for converting data 807 stored in the memory 803 into text, graphics, and/or moving images (as appropriate) shown on the display device 815.

The various components of the computer system 819 may be coupled together by one or more buses, which may include a power bus, a control signal bus, a status signal bus, a data bus, etc. For the sake of clarity, the various buses are illustrated in FIG. 8 as a bus system 819.

One or more specific embodiments of the present disclosure are described herein. These described embodiments are examples of the presently disclosed techniques. Additionally, in an effort to provide a concise description of these embodiments, not all features of an actual embodiment may be described in the specification. It should be appreciated that in the development of any such actual implementation, as in any engineering or design project, numerous embodiment-specific decisions will be made to achieve the developers' specific goals, such as compliance with system-related and business-related constraints, which may vary from one embodiment to another. Moreover, it should be appreciated that such a development effort might be complex and time consuming, but would nevertheless be a routine undertaking of design, fabrication, and manufacture for those of ordinary skill having the benefit of this disclosure.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. For example, any element described in relation to an embodiment herein may be combinable with any element of any other embodiment described herein. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A method for post-birth recovery, comprising:
applying an electromagnetic (EM) field emitter of a pulsed electromagnetic field (PEMF) device to an abdomen of a patient;
receiving an initiating signal;
performing a recovery cycle, including:
setting a plurality of frequency combinations for a plurality of EM fields emitted by the EM field emitter, each frequency combination of the plurality of frequency combinations including a response frequency, a target frequency, and an associated frequency combination period, wherein the plurality of frequency combinations include:
a stop bleeding response frequency (18 Hz) having a stop bleeding frequency combination period of at least 193 minutes;
a remove anesthesia response frequency (19 Hz) having a remove anesthesia frequency combination period of at least one minute;
a lidocaine removal response frequency (7 Hz) having a lidocaine removal frequency combination period of at least one minute;
a decrease inflammation response frequency (40 Hz) having a decrease inflammation frequency combination period of at least one minute;
a repair torn and broken tissue response frequency (124 Hz) having a torn and broken frequency combination period of at least two minutes;
a repair trauma response frequency (294 Hz) having a repair trauma frequency combination period of at least one minute;
a paralysis mitigation response frequency (321 Hz) having a paralysis mitigation frequency combination period of at least one minute;
a reduce allergies response frequency (9 Hz) having a reduce allergies frequency combination period of at least one minute;
a reduce pain response frequency (20 Hz) having a reduce pain frequency combination period of at least one minute;
an emotional component response frequency (970 Hz) having an emotional component frequency combination period of at least four minutes;
a relieve pain and stress response frequency (174 Hz) having a relieve pain and stress frequency combination period of at least two minutes; and
a repair DNA response frequency (528 Hz) having a repair DNA frequency combination period of at least two minutes; and
applying the plurality of EM fields using the frequency combination for the associated frequency combination period.

2. The method of claim 1, wherein applying the plurality of EM fields includes applying the plurality of EM fields in order.

3. The method of claim 1, wherein the plurality of frequency combinations includes, for each response frequency:
a skin target frequency (355 Hz);
an immune system target frequency (116 Hz);
an artery target frequency (62 Hz);
a uterus target frequency (34 Hz);
a stomach target frequency (32 Hz);
a connective tissue target frequency (77 Hz);
a muscle system target frequency (46 Hz);
a ureter target frequency (60 Hz);
an oviduct target frequency (4 Hz);
a fascia target frequency (142 Hz);
a lymphatic system target frequency (13 Hz);
a nerve target frequency (396 Hz);
a spinal cord target frequency (10 Hz);
a bladder target frequency (37 Hz);
a large intestine target frequency (85 Hz);
a small intestine target frequency (22 Hz);
a ligaments target frequency (100 Hz);
an endometrium target frequency (155 Hz);
a genitourinary system target frequency (48 Hz); and
a nervous system target frequency (45 Hz).

4. The method of claim 3, wherein the target frequencies are applied in order.

5. The method of claim 4, wherein the target frequencies and the response frequencies are applied within a tolerance of plus or minus 0.3 Hz.

6. The method of claim 1, wherein the EM field emitter applies both the response frequency and the target frequency simultaneously.

7. A method for post-birth recovery, comprising:
applying a first electromagnetic (EM) field using a pulsed electromagnetic field (PEMF) device, the first EM field having a first frequency to induce a first electrical signal having the first frequency in a patient's body, wherein the first electrical signal targets a group of cells; and
applying a second EM field using the PEMF device, the second EM field having a second frequency to induce a second electrical signal having the second frequency in the patient's body, wherein the second electrical signal induces a tissue recovery response in the targeted group of cells, wherein applying the first EM field and applying the second EM field includes applying the first EM field and the second EM field simultaneously.

8. The method of claim 7, wherein the group of cells is located in an abdomen of a patient and the tissue response is to stop bleeding.

9. The method of claim 7, wherein the group of cells is located in an abdomen of a patient and the tissue recovery response is to decrease inflammation.

10. The method of claim 7, wherein the PEMF device has a combined EM field strength of greater than 0.1 Gauss (G).

11. The method of claim 7, wherein applying the first EM field includes applying the first EM field for an application period of less than 15 minutes.

12. The method of claim 7, wherein the group of cells is a first group of cells and the tissue recovery response is a first tissue recovery response, and further comprising:
applying a third EM field using the PEMF device, the third EM field having a third frequency to induce a third electrical signal having the third frequency in the patient's body, wherein the third electrical signal targets a second group of cells; and
applying a fourth EM field using the PEMF device, the fourth EM field having a fourth frequency to induce a fourth electrical signal having the fourth frequency in the patient's body, wherein the fourth electrical signal induces a second tissue recovery response in a third group of cells.

13. A method for post-birth recovery, comprising:
applying a first electromagnetic (EM) field using a pulsed electromagnetic field (PEMF) device, the first EM field having a first frequency to induce a first electrical signal having the first frequency in a patient's body, wherein the first electrical signal targets a group of cells;
applying a second EM field using the PEMF device, the second EM field having a second frequency to induce a second electrical signal having the second frequency in the patient's body, wherein the second electrical signal induces a tissue recovery response in the targeted group of cells, wherein the group of cells is a first group of cells and the tissue recovery response is a first tissue recovery response
applying a third EM field using the PEMF device, the third EM field having a third frequency to induce a third electrical signal having the third frequency in the patient's body, wherein the third electrical signal targets a second group of cells; and
applying a fourth EM field using the PEMF device, the fourth EM field having a fourth frequency to induce a fourth electrical signal having the fourth frequency in the patient's body, wherein the fourth electrical signal induces a second tissue recovery response in a third group of cells, wherein the first EM field, the second EM field, the third EM field, and the fourth EM field are applied simultaneously.

14. A method for post-birth recovery, comprising:
applying an electromagnetic (EM) field emitter connected to a pulsed electromagnetic field (PEMF) device to a patient's abdomen;
performing a recovery cycle with the PEMF device, the recovery cycle including the method of claim 10.

15. The method of claim 14, wherein applying the EM field emitter includes applying the EM field emitter without a medical practitioner.

16. The method of claim 14, wherein applying the EM field emitter includes applying the EM field emitter within 10 cm of the target group of cells.

17. The method of claim 14, wherein performing the recovery cycle includes pressing a single button on the PEMF device, the PEMF device performing the recovery cycle without additional input.

18. The method of claim 14, further comprising tracking total use of the PEMF device.

19. The method of claim 18, further comprising instructing the PEMF device not to perform the recovery cycle if the total use of the PEMF device exceeds a pre-determined cycle limit.

* * * * *